(12) United States Patent
Burrows et al.

(10) Patent No.: US 11,551,801 B2
(45) Date of Patent: Jan. 10, 2023

(54) MEDICATION DISPENSING SYSTEM, DATA-ENABLED MEDICATION BOX HOLDER, AND METHODS FOR REMINDING, MONITORING, TRACKING, AND/OR COMMUNICATING DOSE EVENTS

(71) Applicant: PillScan, LLC, Philadelphia, PA (US)

(72) Inventors: Mark Burrows, Philadelphia, PA (US); Neal Benjamin, Wynnewood, PA (US); Rafi Licht, Philadelphia, PA (US); David Mantelmacher, Penn Valley, PA (US)

(73) Assignee: PillScan, LLC, Philadelphia, PA (US)

( * ) Notice: Subject to any disclaimer, the term of this patent is extended or adjusted under 35 U.S.C. 154(b) by 0 days.

(21) Appl. No.: 17/208,460

(22) Filed: Mar. 22, 2021

(65) Prior Publication Data

US 2021/0225478 A1 Jul. 22, 2021

Related U.S. Application Data

(62) Division of application No. 15/422,139, filed on Feb. 1, 2017, now Pat. No. 10,957,437.

(51) Int. Cl.
*G16H 20/13* (2018.01)
*G16H 40/63* (2018.01)

(52) U.S. Cl.
CPC ............. *G16H 20/13* (2018.01); *G16H 40/63* (2018.01)

(58) Field of Classification Search
CPC ...... G16H 20/13; G16H 40/63; G06F 19/3456; G06F 19/324; G06F 19/3418
See application file for complete search history.

(56) References Cited

U.S. PATENT DOCUMENTS

| 6,471,087 | B1* | 10/2002 | Shusterman | ......... A61B 5/6805 600/300 |
| 6,601,729 | B1 | 8/2003 | Papp | |
| 7,264,136 | B2* | 9/2007 | Willoughby | ............ G07F 11/68 221/13 |
| 8,019,471 | B2 | 9/2011 | Bogash et al. | |
| 8,196,774 | B1* | 6/2012 | Clarke | .................. A61J 7/0409 221/13 |
| 8,849,449 | B2 | 9/2014 | Waugh et al. | |

(Continued)

*Primary Examiner* — Michael Collins
(74) *Attorney, Agent, or Firm* — Ward and Smith, P.A.; Ryan K. Simmons

(57) ABSTRACT

A medication dispensing system, data-enabled medication box holder, and methods for reminding, monitoring, tracking, and/or communicating dose events are disclosed. The data-enabled medication box holder holds a medication box for dispensing medication packets, each of which is tagged with machine-readable medium, wherein the machine-readable medium indicates the contents of the medication packet. The data-enabled medication box holder includes electronics for processing and communicating information about valid dose events and/or dose exception events. Further, a medication adherence system for and method of monitoring a patient's medication adherence and facilitating dose reminder notifications is disclosed. The medication adherence system includes a centralized server for collecting and processing the patient-specific information from the data-enabled medication box holders.

9 Claims, 16 Drawing Sheets

(56) References Cited

U.S. PATENT DOCUMENTS

| | | | |
|---|---|---|---|
| 9,117,010 B2 | 8/2015 | Feldman et al. | |
| 9,351,907 B2 * | 5/2016 | Luoma | A61J 7/04 |
| 9,460,581 B2 | 10/2016 | Niinistö et al. | |
| 9,892,232 B2 | 2/2018 | Feldman et al. | |
| 10,176,663 B2 * | 1/2019 | King | A61J 7/04 |
| 10,957,437 B2 * | 3/2021 | Burrows | G16H 40/63 |
| 2004/0158350 A1 | 8/2004 | Ostergaard et al. | |
| 2005/0061825 A1 | 3/2005 | Willoughby et al. | |
| 2007/0185615 A1 | 8/2007 | Bossi et al. | |
| 2010/0305967 A1 | 12/2010 | Daya et al. | |
| 2010/0312383 A1 | 12/2010 | Naik et al. | |
| 2011/0202174 A1 * | 8/2011 | Bogash | G07F 9/001 700/242 |
| 2012/0253510 A1 * | 10/2012 | Thomas | G07F 17/0092 700/236 |
| 2013/0066463 A1 * | 3/2013 | Luoma | G16H 20/13 700/232 |
| 2014/0350720 A1 * | 11/2014 | Lehmann | A61J 7/0454 221/3 |
| 2016/0355322 A1 | 12/2016 | Burton et al. | |

\* cited by examiner

MEDICATION DISPENSING SYSTEM, DATA-ENABLED MEDICATION BOX HOLDER, AND METHODS FOR REMINDING, MONITORING, TRACKING, AND/OR COMMUNICATING DOSE EVENTS

RELATED PATENT APPLICATIONS:

This application is a divisional of U.S. patent application Ser. No. 15/422,139, filed Feb. 1, 2017, entitled "Medication Dispensing System, Data-Enabled Medication Box Holder, and Methods for Reminding, Monitoring, Tracking, and/or Communicating Dose Events," the entire disclosure of which is incorporated by reference herein in its entirety.

TECHNICAL FIELD

The presently disclosed subject matter relates generally to the field of medication adherence and more particularly to a medication dispensing system, data-enabled medication box holder, and methods for reminding, monitoring, tracking, and/or communicating dose events.

BACKGROUND

Outpatient prescription medication treatments are relied upon heavily for increased quality of life and lower lifetime healthcare costs. Medical experts have long held that taking at least 80% of a prescribed drug is required to achieve desired therapeutic outcomes and lower lifetime healthcare costs. For example, a patient who faithfully takes cholesterol-reducing medicine significantly reduces the likelihood of a coronary event that has attendant cost-intensive medical procedures and diminished quality of life. Outpatients strongly desire to avoid such events and hospital stays, yet only 20% of all outpatients take their prescription medicines according to doctor's instructions.

Increased medication adherence, also known as patient adherence, medication compliance, or patient compliance, benefits the healthcare system by vastly reducing patients' lifetime medical costs while increasing their therapeutic outcomes. Further, market research suggests that patients have a desire to comply, but will not take on the burden of any additional actions or otherwise change their behavior.

Attempts to date to increase patient adherence have involved attaching dosage-reminder devices to containers by pharmacists, patients, or patient's caregivers. These have had no perceivable impact on adherence, principally because such devices increase, rather than lessen, patients' burden in taking medication. These devices rely on patients for programming, record keeping, decanting, or pressing an event button. While variations of such devices have been around for many years, pharmacists have not been rewarded for taking the time to program and attach them and patients have not been willing to pay for and/or otherwise adopt them.

SUMMARY

In one embodiment, a data-enabled medication box holder is provided. The data-enabled medication box holder may include a housing comprising a compartment configured to at least partially receive a medication box including medication packets; a sensing mechanism integrated with the compartment for sensing the presence or absence of the medication box therein; an electronics module integrated with the housing, wherein the electronics module is configured for providing a reminder at dose time and monitoring, tracking, and communicating valid dose events and/or dose exception events; and one or more indicators electronically coupled to the electronics module. The sensing mechanism may include any one of a proximity sensor, electro-optical sensor, and/or micro-switch. The sensing mechanism may include a micro-switch positioned such that, when present in the compartment, the medication box depresses a pushbutton of the micro-switch, and when the compartment is absent the medication box, the pushbutton of the micro-switch is released. The housing may further include a platform extending from a front portion of the compartment. The platform may extend from a front portion of the compartment such that when the medication box is present, a top surface of the platform is substantially aligned with a slot in the medication box for dispensing the medication packets from the medication box, such that as a medication packet is removed from the slot the medication packet necessarily passes within close proximity of the top surface of the platform. The electronics module may be integrated with the platform. Each medication packet may include machine-readable medium that may include information about the contents of the medication packet. The electronics module may further include a reader/scanner configured to read/scan the machine-readable medium. The reader/scanner may include at least one of an optical window and/or an RFID reader. Dose exception events may include one or more of a missed dose, extra dose, early dose, and/or late dose. A valid dose event may include sensing a presence of the medication box in the data-enabled medication box holder and sensing a presence of machine-readable medium of the medication packet and capturing the contents thereof. The electronics module may further include electrical components for processing data from the sensing mechanism and reader/scanner with respect to a patient's dosing regimen, and for storing and communicating data about valid dose events and/or dose exception events. The electronics module may include control electronics that includes a communications interface; a processor; a real-time clock; the sensor mechanism; one or more indicators; and/or a reader/scanner. The processor may include data storage for storing one or more of a patient's dosing regimen; a dose detection algorithm; and/or actual dose data. The control electronics may be configured for providing a reminder at dose time, detecting valid dose events, and/or processing and communicating data about valid dose events and/or dose exception events. The one or more indicators may include light-emitting diodes (LED).

In another embodiment, a data-enabled medication dispensing system is provided. The data-enabled medication dispensing system may include a data-enabled medication box holder, which may including a housing including a compartment configured to at least partially receive a medication box including medication packets having machine-readable medium; a sensing mechanism integrated with the compartment for sensing the presence or absence of the medication box therein; an electronics module integrated with the housing, wherein the electronics module is configured for providing a reminder at dose time and monitoring, tracking, and communicating valid dose events and/or dose exception events; and one or more indicators electronically coupled to the electronics module. The data-enabled medication dispensing system may further include a medication box received in the compartment; and a server in communication with the electronics module of the medication box holder, wherein the server is configured for collecting and processing patient-specific information communicated from the electronics control module of the data-enabled medication box holder. The server may include a medication adherence application and a database, wherein the database stores one or more of prescription data, summary reports, and/or exception reports.

In yet another embodiment, a method of determining a valid dose event using a data-enabled medication dispensing system is provided. The method may include providing a data-enabled medication box holder, the data-enabled medication box holder may include a housing, the housing including a compartment configured to at least partially receive a medication box including medication packets having machine-readable medium; a sensing mechanism integrated with the compartment for sensing the presence or absence of the medication box therein; an electronics module integrated with the housing, wherein the electronics module is configured for providing a reminder at dose time and monitoring, tracking, and communicating valid dose events and/or dose exception events, and wherein the electronics module comprises a reader/scanner configured to read the machine-readable medium of the medication packets; and one or more indicators electronically coupled to the electronics module. The method may further include monitoring the data-enabled medication box holder for pre-defined valid dose event criteria, wherein the pre-defined valid dose event criteria may include determining if a medication box is present in the data-enabled medication box holder and reading/scanning the machine-readable medium of the medication packet and capturing the contents thereof; determining whether the data-enabled medication box holder has met the pre-defined criteria for the valid dose event; and recording the valid dose event upon determining the pre-defined criteria for the valid dose event is met.

In still yet another embodiment a method of using a data-enabled medication box holder for reminding at dose time and monitoring, tracking, and communicating valid dose events and/or dose exception events is provided. The method may include preparing the data-enabled medication box holder for use wherein the data-enabled medication box holder may include a housing, the housing including a compartment configured to at least partially receive a medication box that may include medication packets having machine-readable medium; a sensing mechanism integrated with the compartment for sensing the presence or absence of the medication box therein; an electronics module integrated with the housing, wherein the electronics module is configured for providing a reminder at dose time and monitoring, tracking, and communicating valid dose events and/or dose exception events, and wherein the electronics module may include a reader/scanner configured to read the machine-readable medium of the medication packets; and one or more indicators electronically coupled to the electronics module. The method may further include monitoring valid dose event criteria and medication adherence; determining whether a valid dose event has occurred, wherein the valid dose event may include sensing the medication box is present in the data-enabled medication box holder and reading/scanning the machine-readable medium of the medication packet and capturing the contents thereof; and recording actual dose event data. Preparing the data-enabled medication box holder for use may include one or more of programming a patient's dosing regimen into a processor of the data-enabled medication box holder; and inserting a medication box into the data-enabled medication box holder. Monitoring valid dose event criteria and medication adherence may include the processor receiving and interpreting data from one or more of the patient's dosing regimen; a dose detection algorithm; a real-time clock; whether and when valid dose events occur and whether they are in compliance with/adherent to dosing instructions stored in the patient's dosing regimen. The one or more indicators may be capable of being monitored by a patient, and may be configured to indicate to the patient at least one of, time to take a dose, a dose has been missed, and/or time for a prescription refill. The method may further include transmitting data from the data-enabled medication box holder to an external computing device using a communications interface. The data from the data-enabled medication box holder may be transmitted to one or more of a patient, caretaker, pharmacist, and/or an authorized party via a communications interface.

BRIEF DESCRIPTION OF THE DRAWINGS

Figure 1:
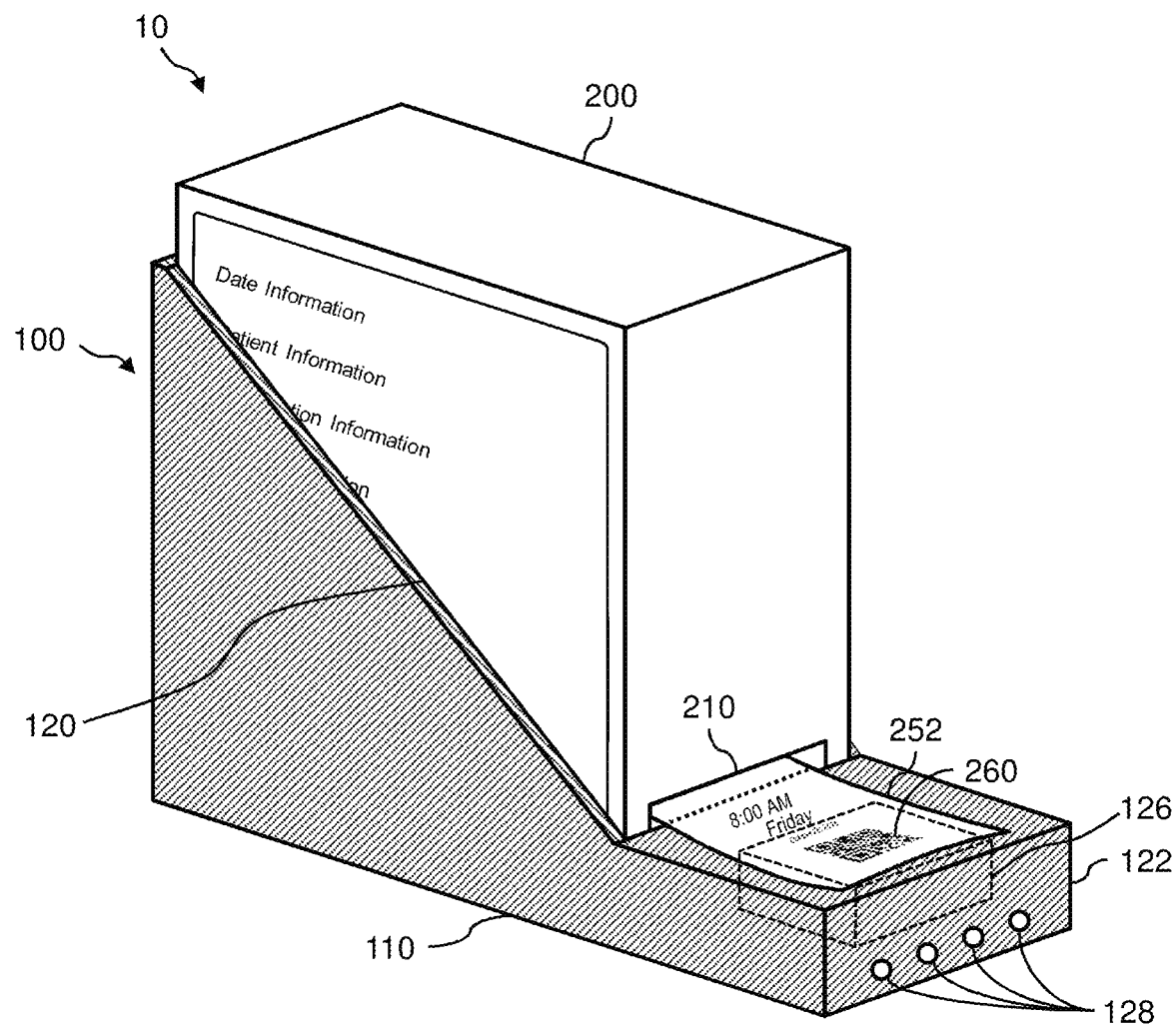
Figure 2:
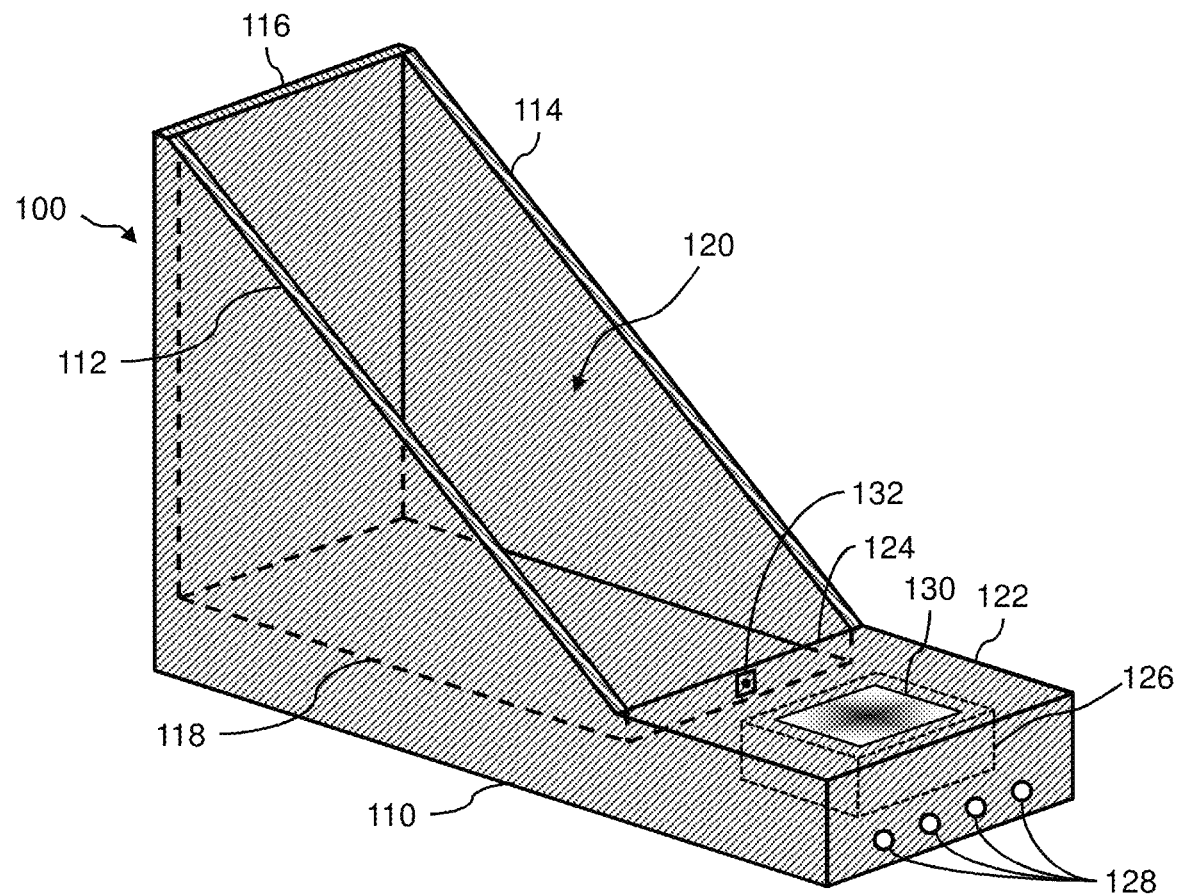
Figure 3:
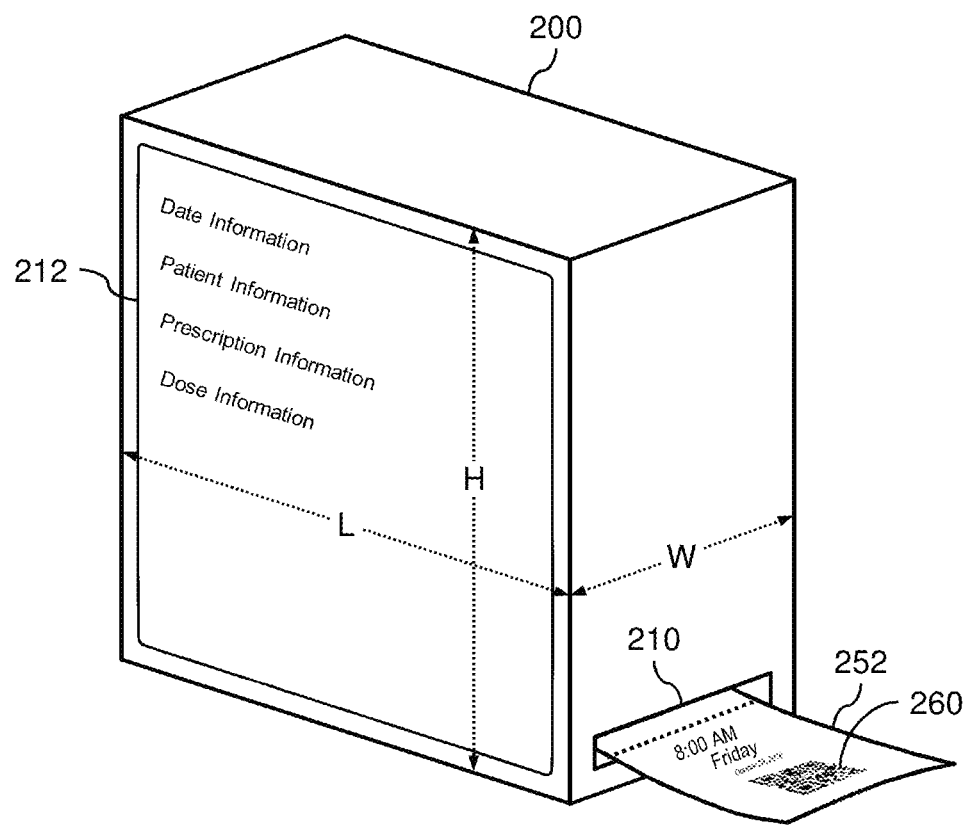
Figure 4:
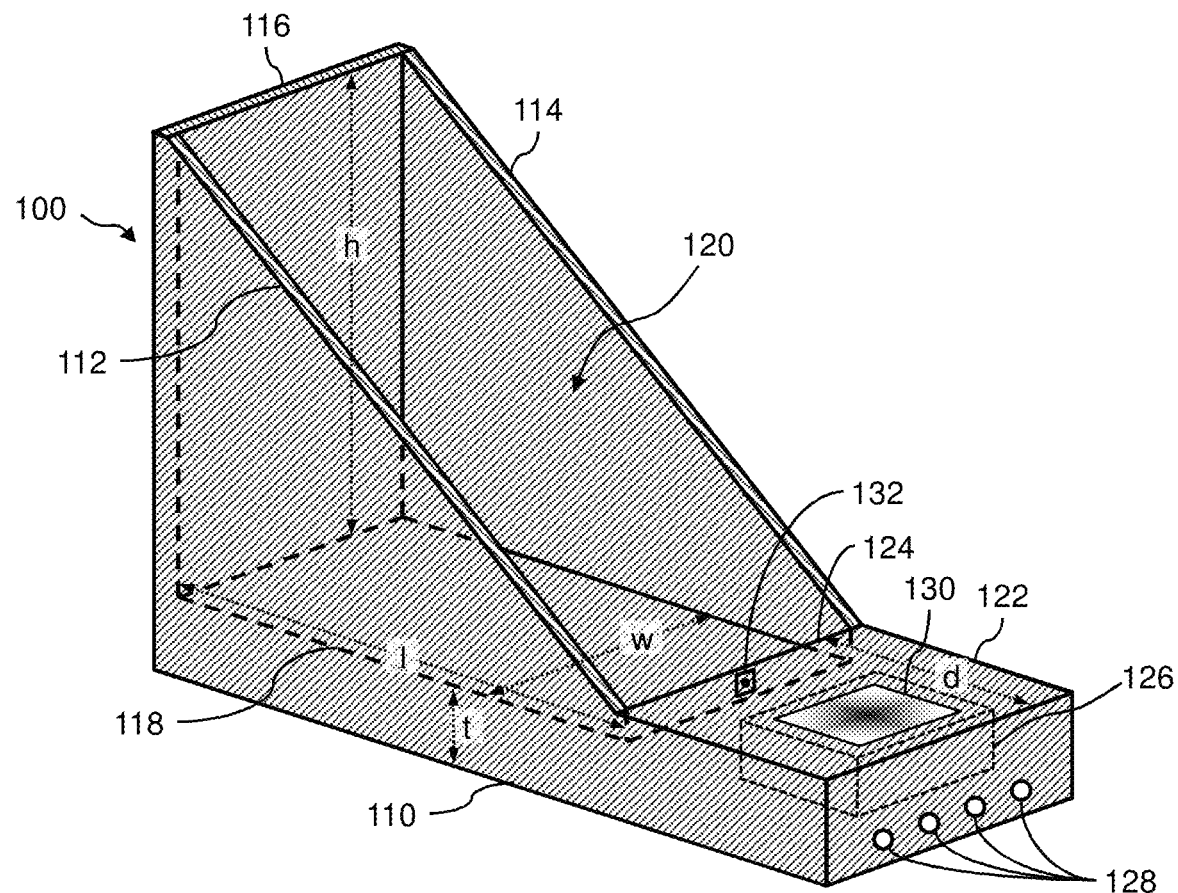
Figure 5A:
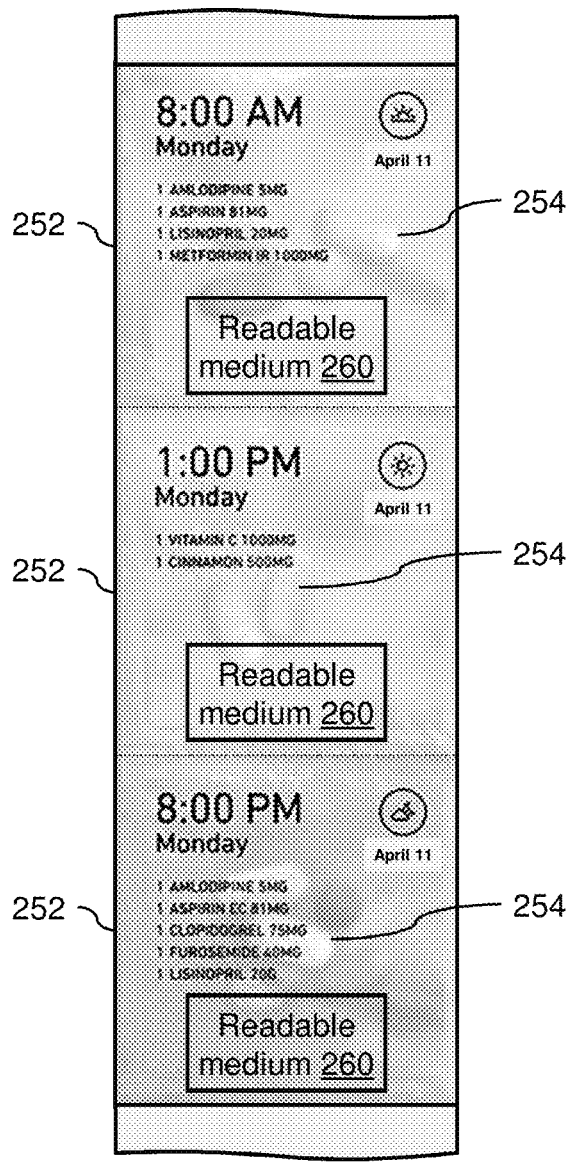
Figure 5B:
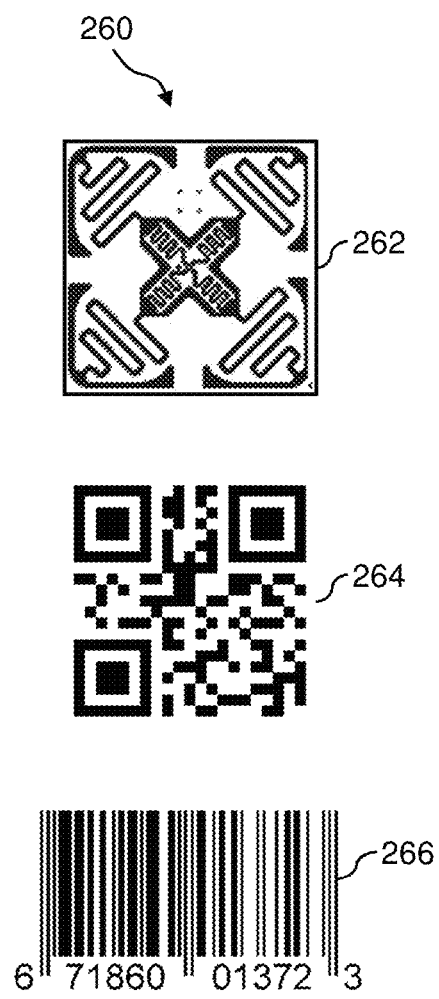
Figure 6:
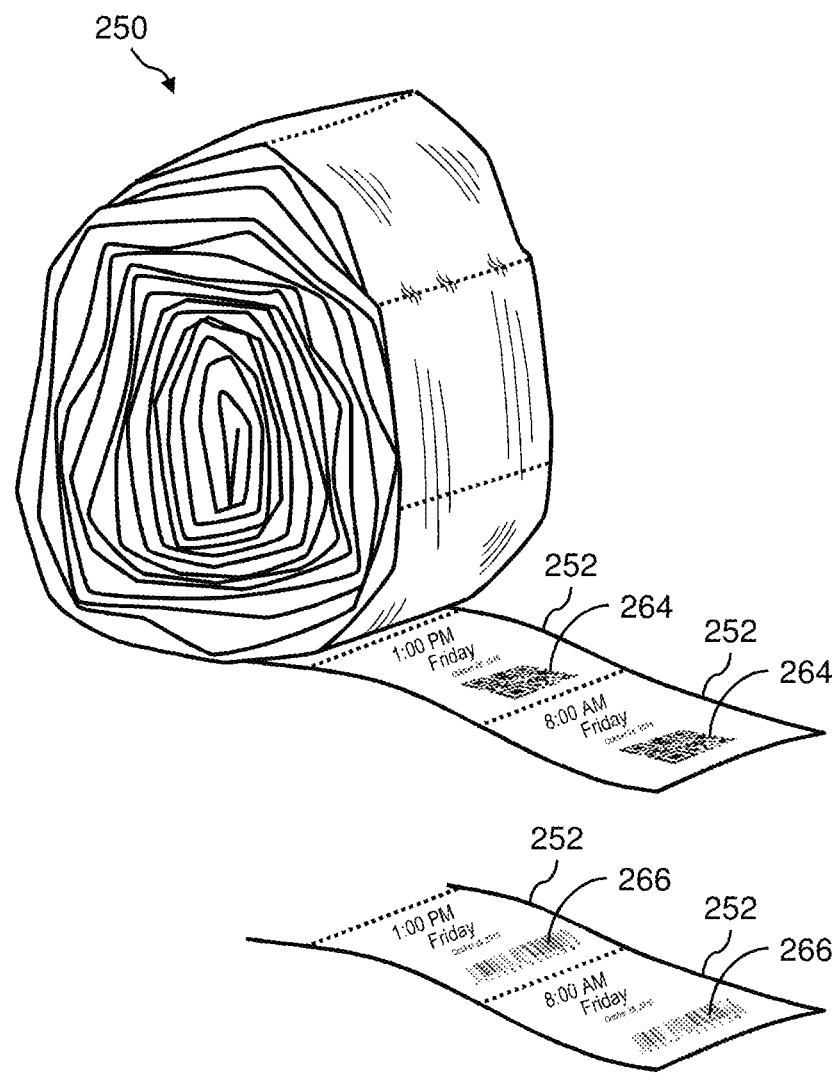
Figure 7:
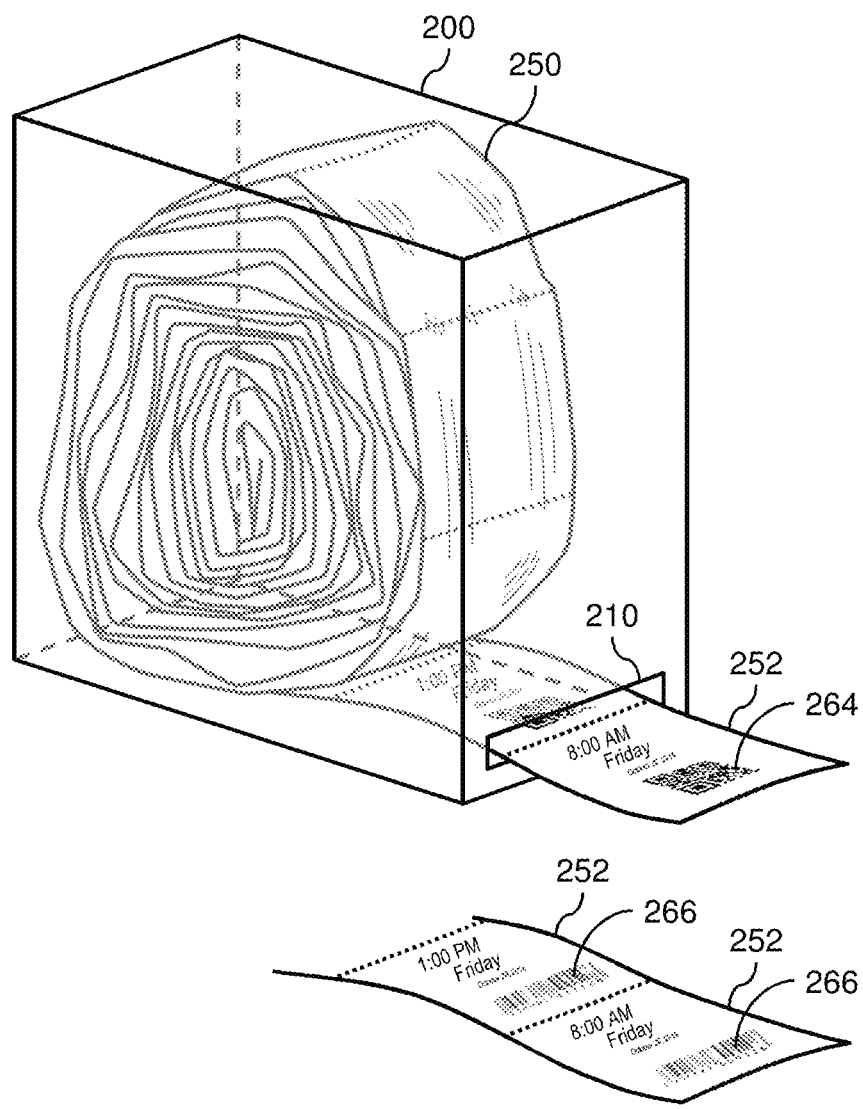
Figure 8:
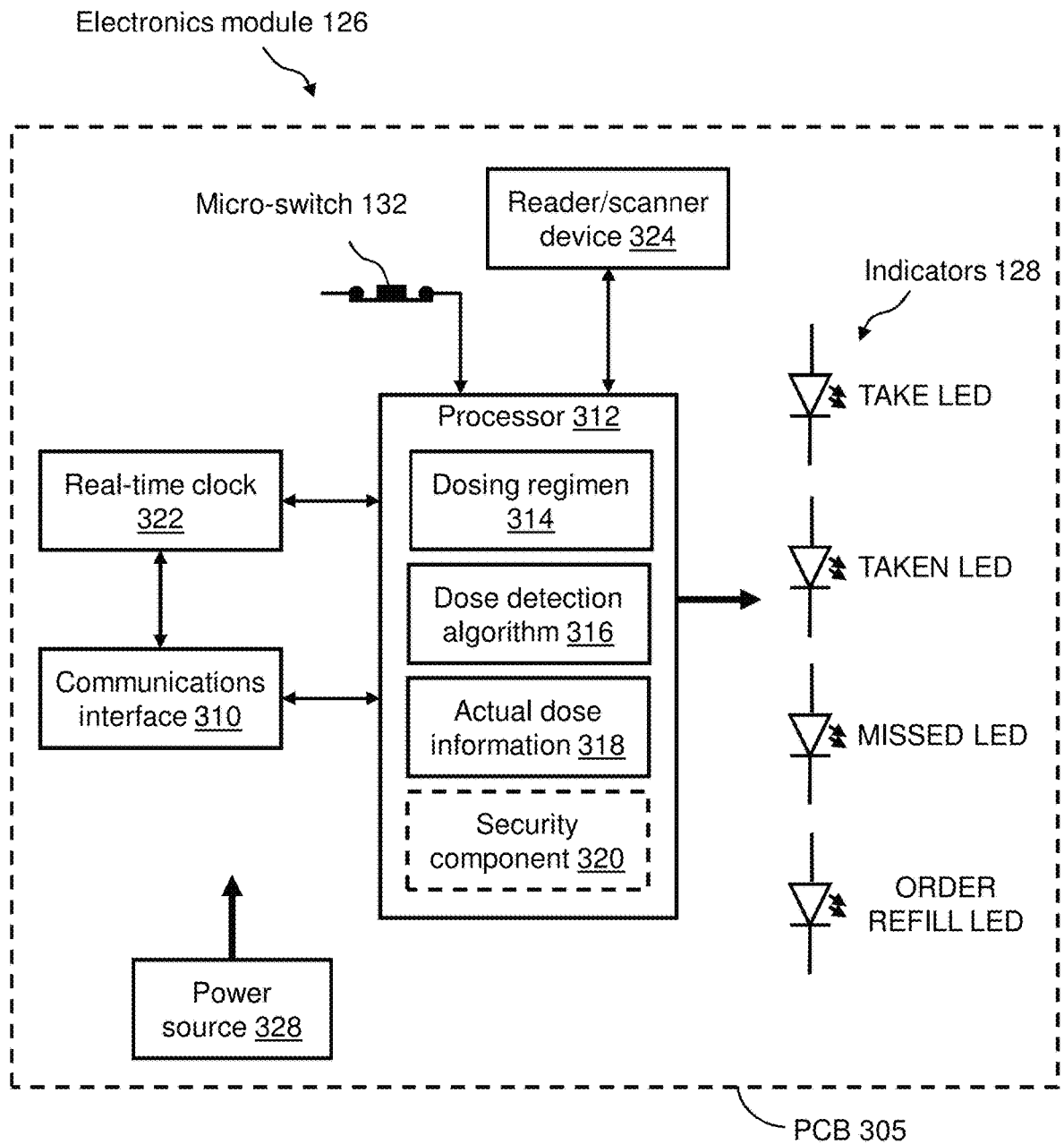
Figure 9:
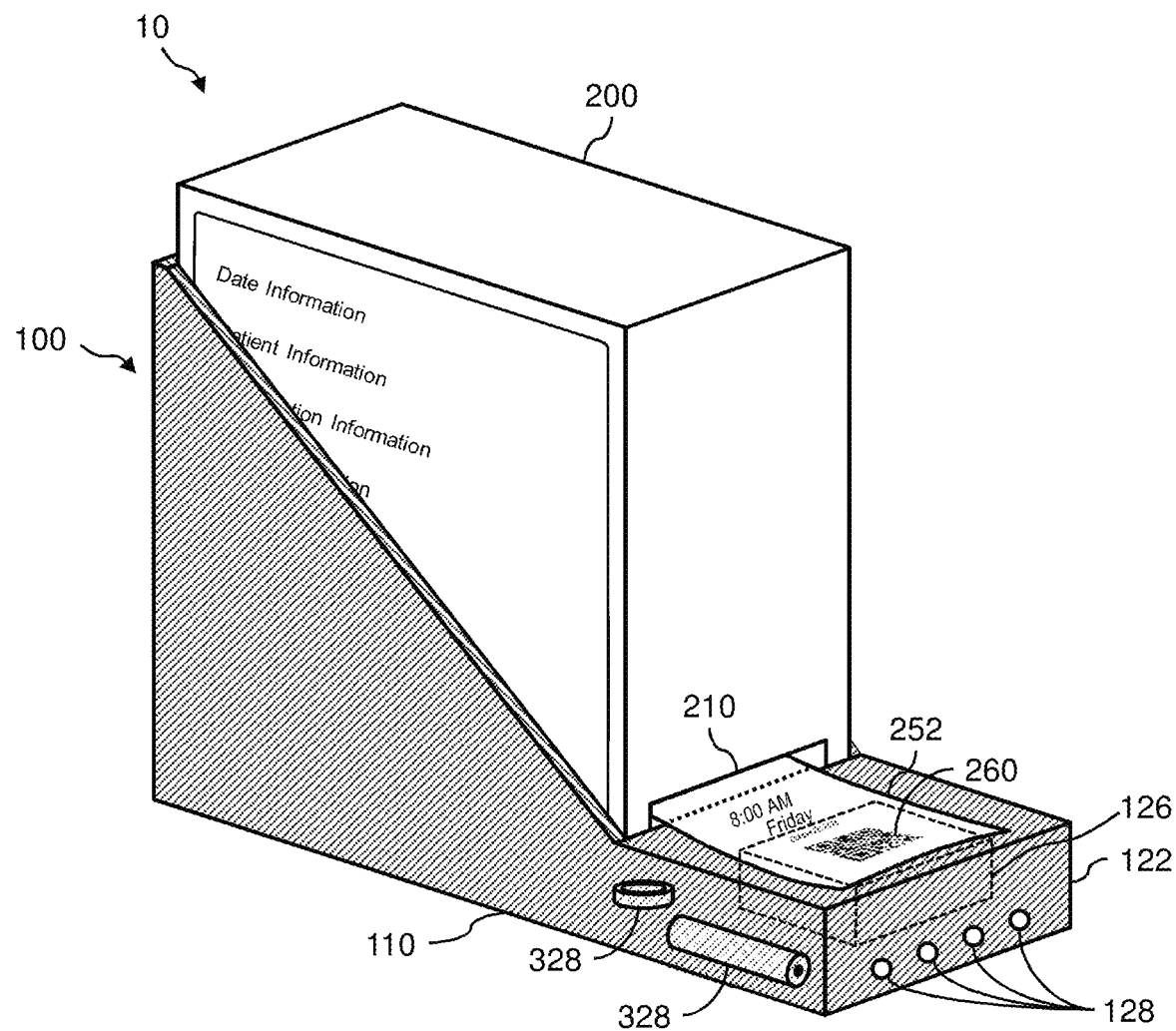
Figure 10:
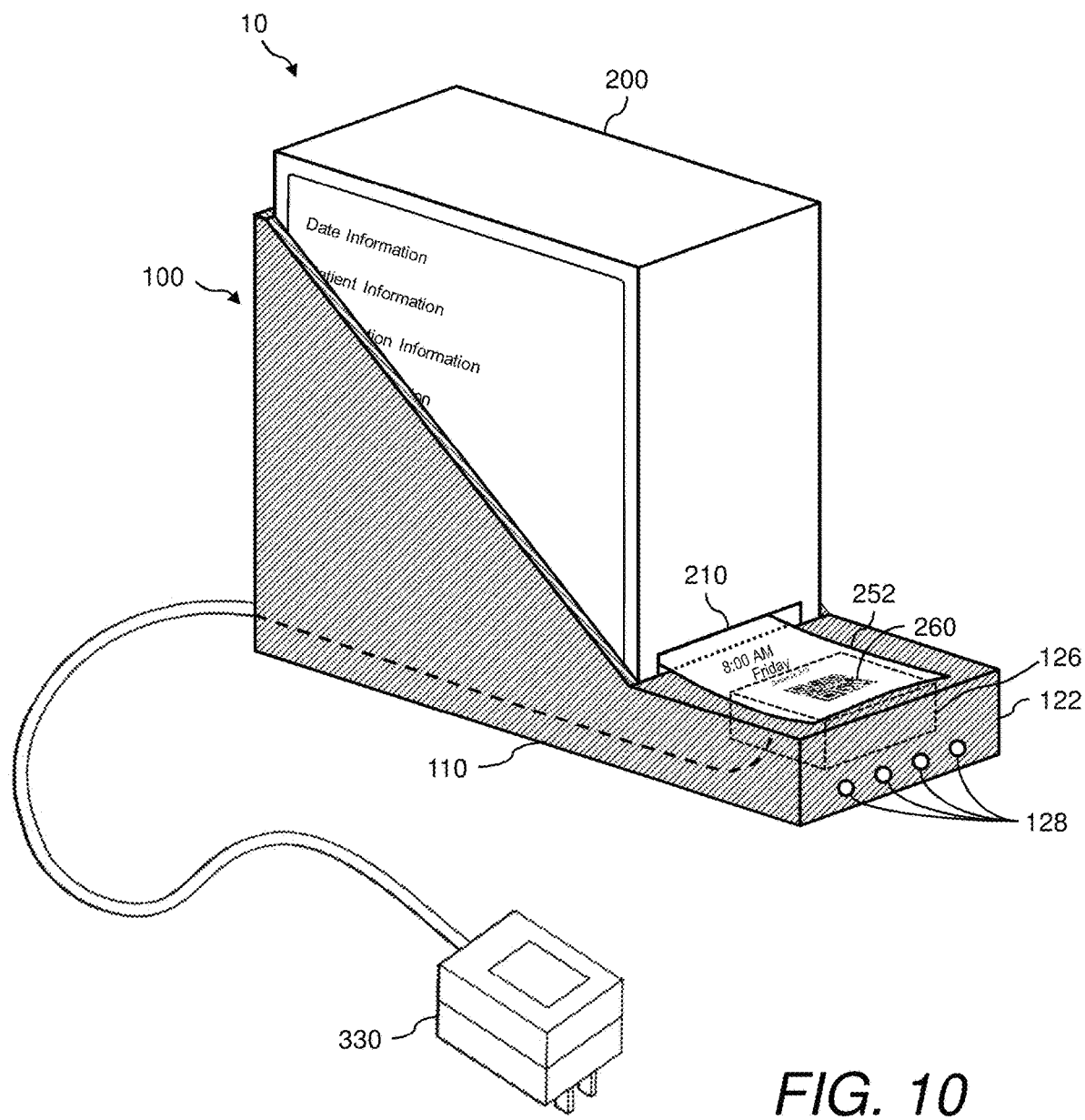
Figure 11:
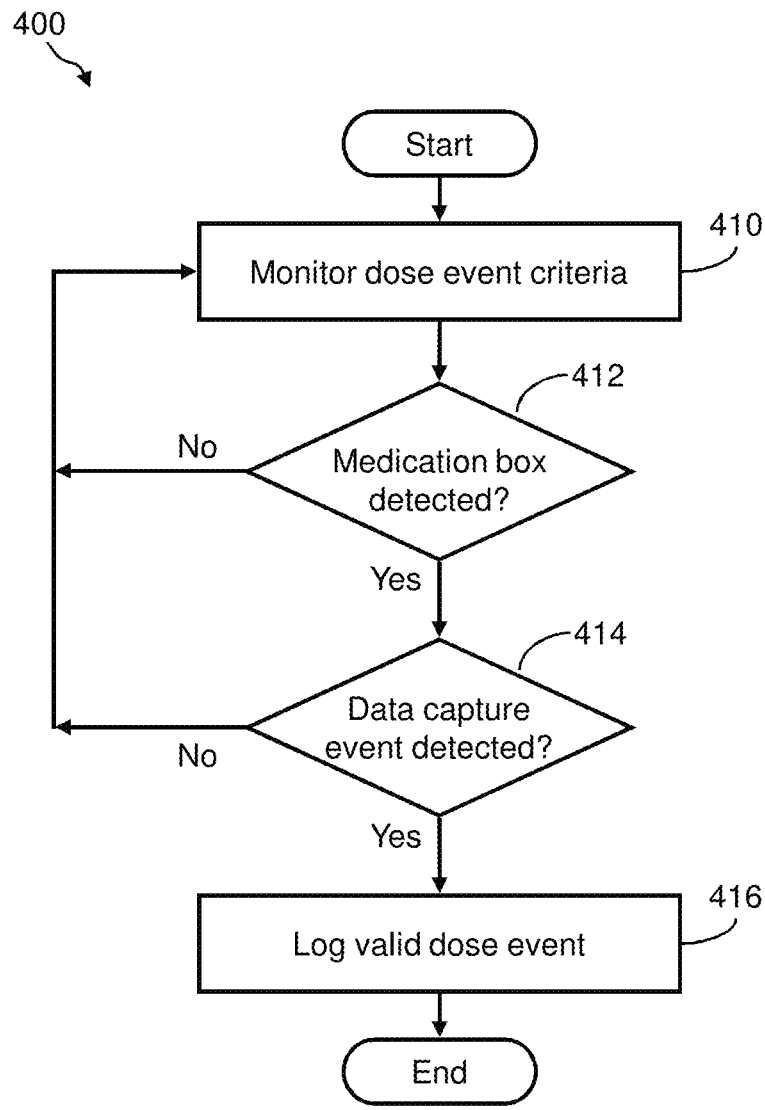
Figure 12:
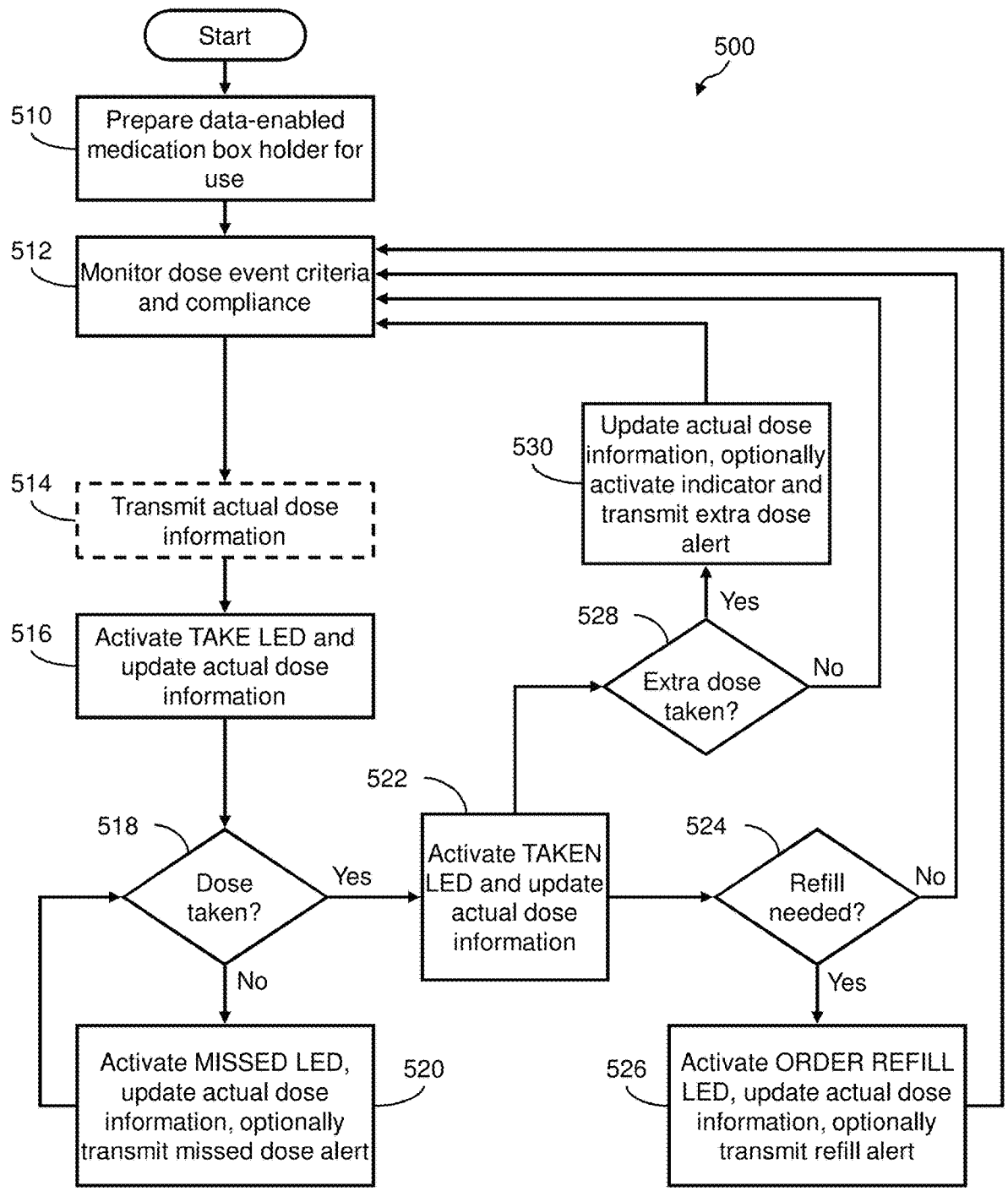
Figure 13:
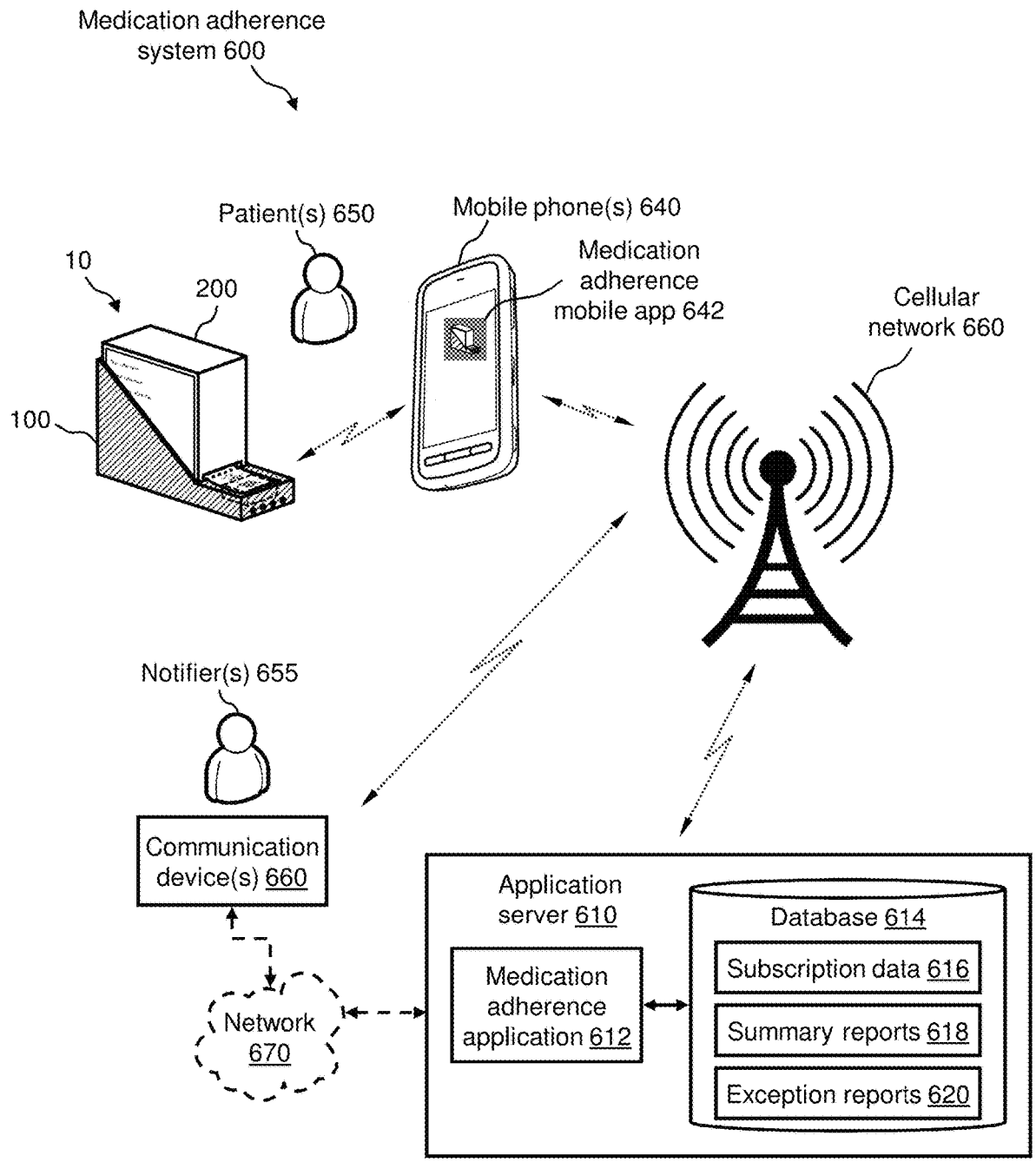
Figure 14:
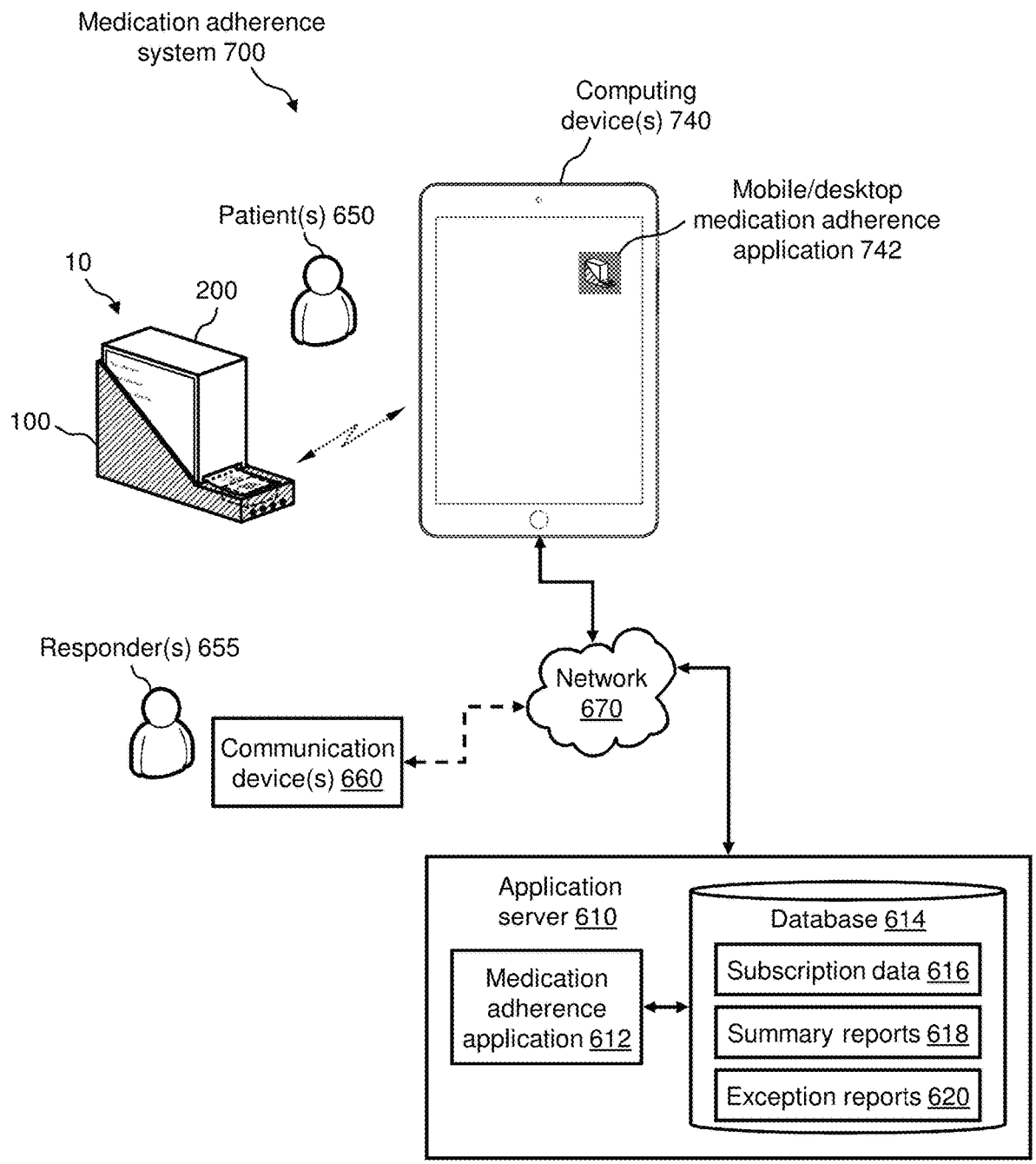
Figure 15:
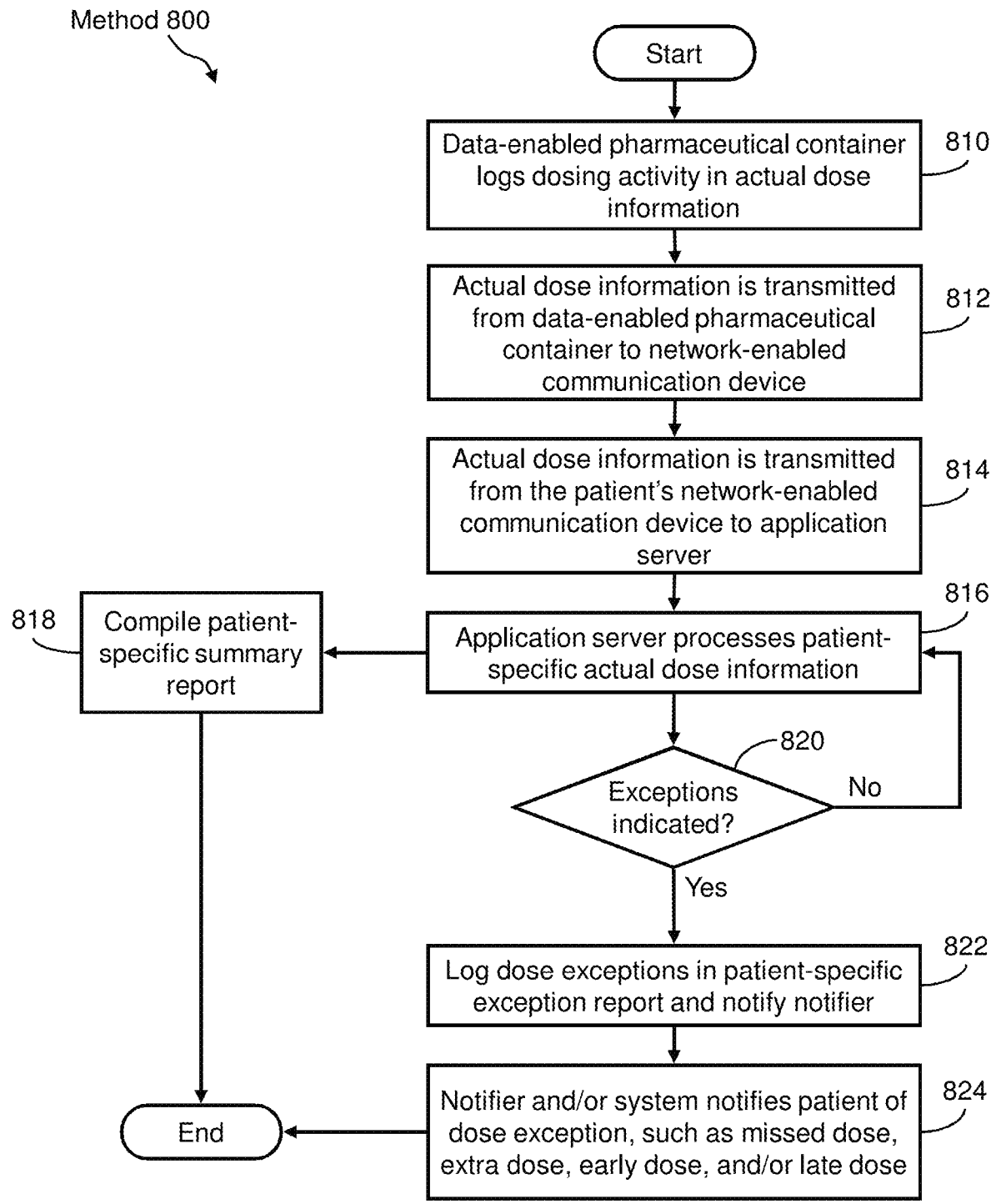
Figure 16:
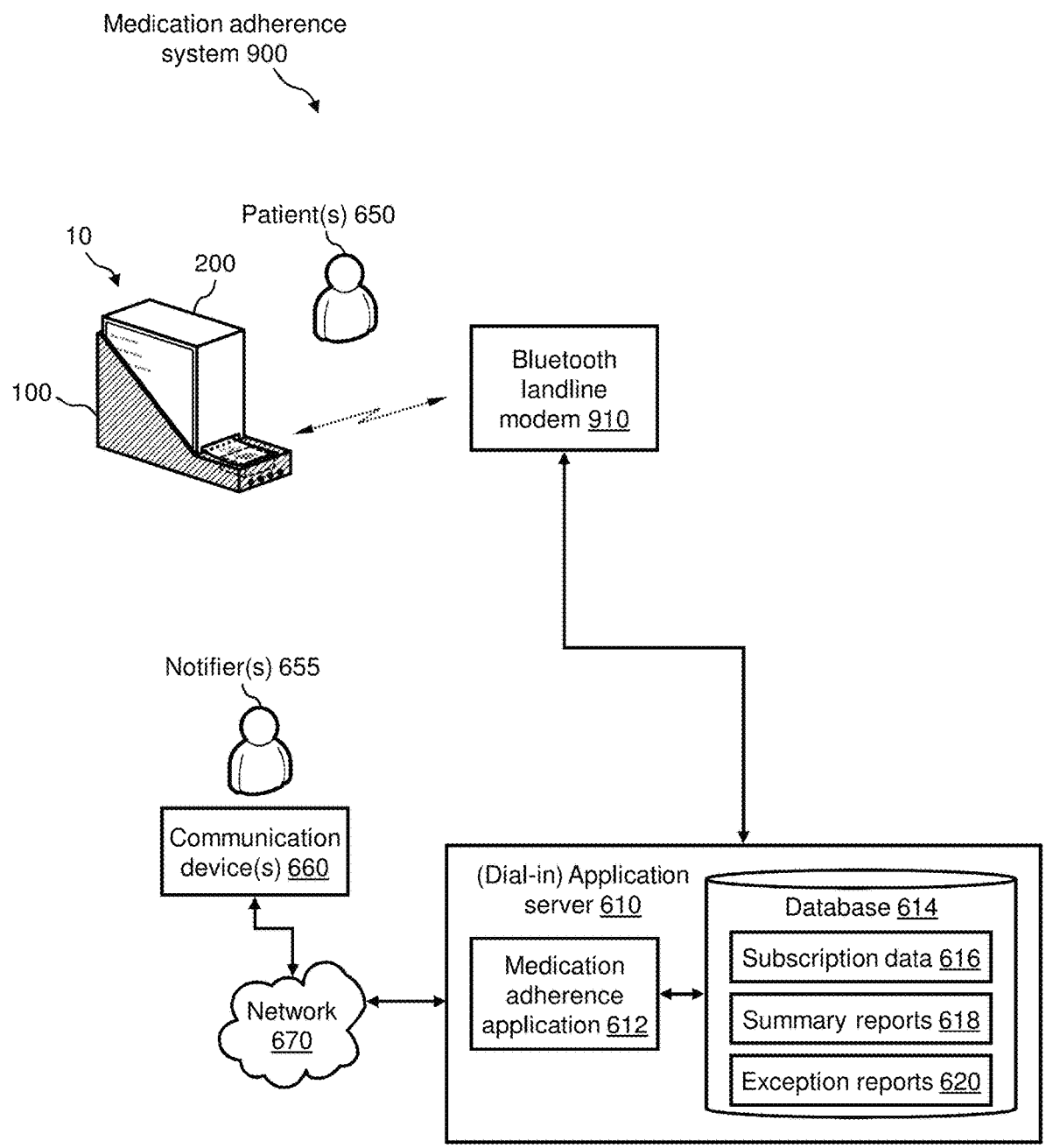

Having thus described the presently disclosed subject matter in general terms, reference will now be made to the accompanying Drawings, which are not necessarily drawn to scale, and wherein:

FIG. 1 illustrates a perspective view of the presently disclosed medication dispensing system that includes a data-enabled medication box holder and a medication box;

FIG. 2 illustrates a perspective view of the presently disclosed data-enabled medication box holder for reminding, monitoring, tracking, and/or communicating dose events;

FIG. 3 illustrates a perspective view of an example of the medication box that can be used with the presently disclosed data-enabled medication box holder;

FIG. 4 illustrates a perspective view of the presently disclosed data-enabled medication box holder and indicates dimensions;

FIG. 5A illustrates a plan view of an example of medication packets that include readable medium that can be detected and/or tracked using the presently disclosed data-enabled medication box holder;

FIG. 5B shows examples of readable medium that can be used in the presently disclosed data-enabled medication box holder;

FIG. 6 illustrates a perspective view of an example of a roll of medication packets that can be detected and/or tracked using the presently disclosed data-enabled medication box holder;

FIG. 7 illustrates a perspective view of the roll of medication packets in relation to the medication box;

FIG. 8 illustrates a block diagram of an example of control electronics of the presently disclosed data-enabled medication box holder;

FIG. 9 shows an example of the presently disclosed data-enabled medication box that uses battery power;

FIG. 10 shows an example of the presently disclosed data-enabled medication box that is powered using an AC adaptor;

FIG. 11 illustrates a flow diagram of an example of a method of determining a valid dose event using the presently disclosed data-enabled medication box holder;

FIG. 12 illustrates a flow diagram of an example of a method of operation of the presently disclosed data-enabled medication box holder;

FIG. 13 illustrates a block diagram of a medication adherence system for monitoring a patient's medication adherence and facilitating dose reminder notifications according to one embodiment of the invention;

FIG. 14 illustrates a block diagram of a medication adherence system for monitoring a patient's medication adherence and facilitating dose reminder notifications according to another embodiment of the invention;

FIG. 15 illustrates a flow diagram of an example of a method of using the presently disclosed medication adherence system for monitoring a patient's medication adherence and facilitating dose reminder notifications; and FIG. 16 illustrates a block diagram of a medication adherence system for monitoring a patient's medication adherence and facilitating dose reminder notifications according to yet another embodiment of the invention.

DETAILED DESCRIPTION

The presently disclosed subject matter now will be described more fully hereinafter with reference to the accompanying Drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

In some embodiments, the presently disclosed subject matter provides a medication dispensing system, data-enabled medication box holder, and methods for reminding, monitoring, tracking, and/or communicating dose events. The presently disclosed medication dispensing system includes the data-enabled medication box holder and a medication box, wherein the medication box dispenses medication packets and each of the medication packets has machine-readable medium having information about the contents of the medication packet.

The presently disclosed data-enabled medication box holder includes an electronics module that further includes technology for reminding at dose time and tracking and communicating valid dose events and/or dose exception events. Examples of dose exception events include, but are not limited to, missed doses, extra doses, early doses, and late doses.

Namely, the electronics module of the data-enabled medication box holder includes circuitry for reminding at dose time, detecting valid dose events, as well as for processing and communicating information about valid dose events and/or dose exception events. For example, using a dose detection algorithm, a dose event is deemed valid based on (1) sensing the presence of the medication box in the data-enabled medication box holder, and (2) sensing the presence of readable medium and capturing the contents thereof.

An aspect of the data-enabled medication box holder is that it may be used to increase patient adherence with respect to dosing regimens while requiring no additional actions or otherwise changed behavior by the patient, such as programming, record keeping, or decanting of medication from one container into another.

Another aspect of the data-enabled medication box holder is that records of digital information about dose events and/or dose exception events (e.g., missed, extra, early, and late doses) are automatically generated and stored thereon, wherein the digital information can be used to determine periodically or continuously whether the prescribed dosing regimen is being followed.

Yet another aspect of the data-enabled medication box holder is that it includes a communications interface for wired or wireless communication with an external computing device.

The presently disclosed subject matter also provides a medication adherence system for monitoring a patient's medication adherence and facilitating dose reminder notifications. The medication adherence system is based on a network of data-enabled medication box holders, wherein the data-enabled medication box holders provide mechanisms for reminding at dose time, tracking and communicating valid dose events, as well as missed, extra, early, and/or late dose events. The medication adherence system includes a centralized server for collecting and processing the patient-specific information from the data-enabled medication box holders.

FIG. 1 illustrates a perspective view of the presently disclosed medication dispensing system 10 that includes a data-enabled medication box holder 100 and a medication box 200, wherein the medication box 200 holds medication packets that include machine-readable medium. The data-enabled medication box holder 100 can be used for reminding, monitoring, tracking, and/or communicating dose events and/or dose exception events. The data-enabled medication box holder 100 includes a baseplate 110 that supports a compartment 120. The compartment 120 is sized and shaped to hold the medication box 200. More details of the data-enabled medication box holder 100 are shown and described hereinbelow with reference to FIG. 2, FIG. 4, FIG. 9, and FIG. 10.

The medication box 200 can be any medication box (e.g., a cardboard box) for dispensing medication that is organized by date and time. For example, the medication box 200 holds a medication roll 250 (see FIG. 6 and FIG. 7) of medication packets 252, wherein each of the medication packets 252 can be a plastic pouch that may hold multiple medications and is labeled with the prescribed dose date and time. Perforations between adjacent medication packets 252 allow individual medication packets 252 to be easily torn away from the medication roll 250. Accordingly, the medication box 200 is a tape-dispenser style of box, wherein the end of the medication roll 250 is fed out of a slot 210 in the medication box 200. One example of the medication box 200 and medication roll 250 is the PillPack system available from the PillPack Pharmacy (Manchester, NH). In other embodiments, instead of or in addition to perforations between adjacent medication packets 252, the slot 210 can include a serrated edge (not shown) for cutting off medication packets 252 from the medication roll 250.

Further, in the presently disclosed medication dispensing system 10, each of the medication packets 252 in the medication roll 250 has readable medium 260 installed thereon. The readable medium 260 can be any type of machine-readable medium (e.g., a quick response (QR) code, a barcode, a radio-frequency identification (RFID) tag) that can be programed with information about the contents of the medication packet 252. More details of the medication box 200 are shown and described hereinbelow with reference to FIG. 3. More details of the medication roll 250 and medication packets 252 are shown and described hereinbelow with reference to FIG. 5A, FIG. 5B, FIG. 6, and FIG. 7.

In the data-enabled medication box holder 100, a platform 122 is provided at the forward portion of the compartment 120 and in relation to the slot 210 of the medication box 200. An electronics module 126 and certain indicators 128 (e.g., light-emitting diodes (LEDs)) are integrated into the platform 122 of data-enabled medication box holder 100. Further, a digital display (not shown) may be in integrated into the platform 122. The electronics module 126 includes technology that corresponds to the technology of the readable medium 260 of the medication packets 252 in the medication box 200. Namely, the electronics module 126 includes any technology that can be used to read/scan the contents of the readable medium 260 of the medication packets 252. Optionally, depending on the type of reading/scanning technology in the electronics module 126, an optical window 130 can be provided at the upper surface of platform 122. The optical window 130 can be, for example, a glass window or an uncovered opening.

Further, the electronics module 126 includes technology for storing, processing, and/or communicating information about the contents of the medication packets 252. For example, the electronics module 126 can be used for processing information about the contents of the medication packets 252 with respect to the patient's dosing regimen, and for storing and communicating information about doses taken, doses missed, extra doses, early doses, and/or late doses. More details of the electronics module 126 are shown and described hereinbelow with reference to FIG. 8.

FIG. 2 illustrates a perspective view of the presently disclosed data-enabled medication box holder 100 for reminding, monitoring, tracking, and/or communicating dose events. The data-enabled medication box holder 100 includes the baseplate 110, a first sidewall 112, a second sidewall 114, and a back wall 116. The first sidewall 112, the second sidewall 114, and the back wall 116 form the compartment 120, wherein the upper surface of the baseplate 110 forms a floor 118 of the compartment 120. The compartment 120 opens toward the platform 122. The plane of the upper surface of the platform 122 is slightly raised in relation to the plane of the floor 118 of the compartment 120 to form a lip or front wall 124. In one example, the side profiles of the first sidewall 112 and the second sidewall 114 taper from the back wall 116 toward the platform 122. However, this is exemplary only. The side profiles of the first sidewall 112 and the second sidewall 114 can be any other shapes, such as square or rectangular, as long as they provide suitable sidewalls for the compartment 120. The data-enabled medication box holder 100 can be formed of any suitably rigid, lightweight material, such as molded plastic or metal (e.g., aluminum, stainless steel). The baseplate 110 and/or the platform 122 can be hollow or solid members.

Further, a sensing mechanism can be integrated into the compartment 120 to sense the absence or presence of the medication box 200 therein. Examples of sensing mechanisms include, but are not limited to, proximity sensors (e.g., infrared-based), electro-optical sensors (e.g., optical position sensors, photoelectric sensors), micro-switches, and the like. In one example, a micro-switch 132 can be integrated into the front wall 124 of the compartment 120 of the platform 122 of data-enabled medication box holder 100. The micro-switch 132 can be used to detect the presence of the medication box 200 in the compartment 120 of the data-enabled medication box holder 100. Namely, when present in the compartment 120, the medication box 200 depresses a pushbutton of the micro-switch 132. By contrast, when the compartment 120 is absent the medication box 200, the pushbutton of the micro-switch 132 is released. In other embodiments, the micro-switch 132 can be integrated into any portion of the compartment 120; namely, into the first sidewall 112, the second sidewall 114, the back wall 116, the floor 118, and/or the front wall 124 of the compartment 120. In one example, the micro-switch 132 is a side-actuated momentary contact switch, such as the SDS005 side-actuated detect switch, available from ITT Corporation (White Plains, N.Y.).

FIG. 3 illustrates a perspective view of an example of the medication box 200 that can be used with the presently disclosed data-enabled medication box holder 100. The medication box 200 has a length L, a width W, and a height H. In one example, the medication box 200 is the PillPack medication box that has a length L of about 6 inches, a width W of about 3 inches, and a height H of about 6 inches. Further, a label 212 can be affixed to the side of the medication box 200. Printed on the label 212 can be, for example, date information, patient information, prescription information, and dose regimen information.

The data-enabled medication box holder 100 is sized according to the size of the medication box 200. For example, FIG. 4 shows that the compartment 120 of the data-enabled medication box holder 100 has a length l, a width w, and a height h. The length l of the compartment 120 substantially corresponds to the length L of the medication box 200. The width w of the compartment 120 substantially corresponds to the width W of the medication box 200. The height h of the compartment 120 can substantially correspond to the height H (or some portion thereof) of the medication box 200. Further, in one example, the first sidewall 112, the second sidewall 114, and the back wall 116 of the compartment 120 can be about ⅛ inches thick. In one example, the thickness t of the baseplate 110 can be, for example, from about ¼ inch to about 1 inch. In one example, the height of the platform 122 can be from about ¼ inch to about ½ inch greater than the thickness t of the baseplate 110.

FIG. 5A illustrates a plan view of an example of the medication packets 252 that include readable medium 260 that can be detected and/or tracked using the presently disclosed data-enabled medication box holder 100. In one example, the medication packets 252 is the PillPack brand pouches. In the medication roll 250, the medication packets 252 are, for example, flexible plastic packets or pouches that can hold pills or tablets 254, wherein the pills or tablets 254 can be multiple types of prescription and/or nonprescription medication. The contents of each of the medication packets 252 is unique to a certain patient's prescriptions. The medication packets 252 are organized in order by date and time based on when the medication should be taken. For example, FIG. 5A shows a portion of the medication roll 250 that includes three medication packets 252—a first medication packet 252 holding pills or tablets 254 to be taken on Monday, April 11 at 8:00 am; a second medication packet 252 holding pills or tablets 254 to be taken on Monday, April 11 at 1:00 pm; and a third medication packet 252 holding pills or tablets 254 to be taken on Monday, April 11 at 8:00 pm. In this example, the contents of the three medication packets 252 may be the same or different.

Further, each of the three medication packets 252 has readable medium 260 affixed thereto, wherein the readable medium 260 is programmed to indicate the contents of its corresponding medication packet 252. The contents of each readable medium 260 may include, for example, but is not limited to, prescription information, patient information, prescribing physician information, date and time information, medication and dose regimen information, and the like.

Namely, the contents of the readable medium 260 of the first medication packet 252 is unique to the first medication packet 252. The contents of the readable medium 260 of the second medication packet 252 is unique to the second medication packet 252. The contents of the readable medium 260 of the third medication packet 252 is unique to the third medication packet 252, and so on.

FIG. 5B shows examples of different types of the readable medium 260 that can be used in the presently disclosed data-enabled medication box holder 100. Namely, an RFID tag 262 is one example of the readable medium 260. A QR code 264 is another example of the readable medium 260. A barcode 266 is yet another example of the readable medium 260.

FIG. 6 illustrates a perspective view of an example of the medication roll 250 of the medication packets 252 that can be detected and/or tracked using the presently disclosed data-enabled medication box holder 100. In one example, the medication roll 250 is the PillPack medication roll and the medication packets 252 is the PillPack pouches. Further, the first packet (i.e., the leader packet) in the medication roll 250 may not be a medication packet 252 holding medication. Rather, the leader packet may be used, for example, to trigger or activate the electronics module 126. FIG. 7 shows the medication roll 250 of the medication packets 252 in relation to the medication box 200. In one example, the medication roll 250 is a 30-day roll of pills or tablets 254 arranged in multiple medication packets 252. The medication packets 252 can be separated from the medication roll 250 by tearing along a perforation. The medication packets 252 are organized in the medication roll 250 in order by date and time based on when the medication should be taken. By way of example, FIG. 6 and FIG. 7 show medication packets 252 that include QR codes 264 or barcodes 266.

Further, FIG. 7 shows the leading edge of the medication roll 250 feeding through the slot 210 of the medication box 200. The user can manually pull the medication packets 252 from the slot 210 and tear off the medication packet 252 that is needed. The medication roll 250 unrolls with each pull. However, the medication box 200 is not limited to dispensing the medication packets 252 by manual pulling. Power-assist mechanisms are possible in combination with the medication box 200. In some embodiments, the medication roll 250 can be provided on an axel or spool, the ends of which can be accessible through the sides of the medication box 200. Then, a motor drive mechanism (not shown) in the data-enabled medication box holder 100 couples to the axel or spool to impart rotating motion to the medication roll 250 in the medication box 200. In another example, instead of coupling to the axel or spool, a motorized pinch roller on the platform 122 can engage with the medication roll 250 as the medication packets 252 exit the slot 210. In these motorized examples, a user pushes a button or lever (not shown) to activate a motor mechanism (not shown) that ejects the medication packets 252 from the slot 210 of the medication box 200. In one example, the motor runs for whatever duration the user holds the button. In another example, whenever the user pushes the button the motor runs only until the readable medium 260 is read. In other embodiments, the data-enabled medication box holder 100 can include a manual push-paddle lever mechanism (not shown), such as those used in paper towel dispensers, that couples to the axel or spool to impart rotating motion to the medication roll 250 in the medication box 200. In yet other embodiments, the drive mechanism can be integrated into the medication box 200 instead of into the data-enabled medication box holder 100.

FIG. 8 illustrates a block diagram of an example of the electronics module 126 of the data-enabled medication box holder 100 for reminding at dose time, detecting valid dose events, as well as for processing and communicating information about valid dose events and/or dose exception events (e.g., missed, extra, early, and late doses). The electronics module 126 can be circuitry that is implemented, for example, on a printed circuit board (PCB) 305. In this example, the electronics module 126 includes a communications interface 310, a processor 312, a real-time clock 322, the micro-switch 132, a reader/scanner device 324, and the one or more indicators 128. The processor 312 further includes the patient's dosing regimen 314, a dose detection algorithm 316, actual dose information 318, and optionally a security component 320.

The components of the electronics module 126 are powered by a power source 326. In one example and referring now to FIG. 9, the power source 326 of the data-enabled medication box holder 100 can be one or more batteries 328, wherein the batteries 328 can be any standard cylindrical battery, such as quadruple-A, triple-A, or double-A, or a battery from the family of button cell and coin cell batteries. A specific example of a battery 328 is the CR2032 coin cell 3-volt battery. In another example and referring now to FIG. 10, the power source 326 of the data-enabled medication box holder 100 can be a standard AC adaptor 330 that converts a standard 110 VAC input to a certain DC output voltage and at a certain power rating.

Referring now again to FIG. 8, the communications interface 310 may be any wired and/or wireless communication interface for connecting to a network (not shown) and by which information may be exchanged (i.e. bidirectional communication) with other devices connected to the network. Examples of wired communication interfaces may include, but are not limited to, USB ports, RS232 connectors, RJ45 connectors, Ethernet, and any combinations thereof. Examples of wireless communication interfaces may include, but are not limited to, an Intranet connection, Internet, cellular networks, ISM, Bluetooth® technology, Wi-Fi, Wi-Max, IEEE 302.11 technology, radio frequency (RF), Infrared Data Association (IrDA) compatible protocols, Local Area Networks (LAN), Wide Area Networks (WAN), Shared Wireless Access Protocol (SWAP), any combinations thereof, and other types of wireless networking protocols. Examples of information facilitated by the communications interface 310 include the transmission of the dosing regimen 314 and the actual dose information 318. Other examples of information facilitated by the communications interface 310 is the transmission of a "missed dose alert", a "refill alert", and an "extra dose alert" to/from the patient, to/from a caretaker, or to/from any other authorized party.

The processor 312 is used to manage the overall operations of the data-enabled medication box holder 100 with respect to reminding at dose time and tracking and communicating valid dose events and/or dose exception events (e.g., missed, extra, early, and late doses). The processor 312 can be any standard controller or microprocessor device that is capable of executing program instructions. A certain amount of data storage (not shown) may be associated with the processor 312. In one example, the processor 312 is the PIC18LF14K50 Microcontroller, available from Microchip Technology, Inc (Chandler, Ariz.).

Using the communications interface 310, a patient's dosing regimen 314 can be loaded into the processor 312. The dosing regimen 314 can be any information about the patient's prescribed medication and dosing regimen, which may include one or multiple types of medications. One example of the dosing regimen 314 that includes one type of medication only is as follows—one 50-mg dose daily of a levothyroxine (e.g., one dose upon waking). Another example of the dosing regimen 314 that includes one type of medication only is as follows—two 50-mg doses daily of levothyroxine (e.g., one dose every 12 hours). Yet another example of the dosing regimen 314 that includes one type of medication only is as follows—three 50-mg doses daily of levothroxine (e.g., one dose upon waking, one mid-day dose, and one dose at bedtime). In the dosing regimen 314, one dose upon waking can mean, for example, 8 am; one mid-day dose can mean, for example, 1 pm; one dose at bedtime can mean, for example, 8 pm; and one dose every 12 hours can mean, for example, 8am and 8 pm. However, these times can vary.

By contrast, an example of the dosing regimen 314 that includes multiple types of medications is as follows—one 50-mg dose daily of a first medication (e.g., one mid-day dose), plus two 200-mg doses daily of a second medication (e.g., one dose every 12 hours), plus three 10-mg doses daily of a third medication (e.g., one dose upon waking, one mid-day dose, and one dose at bedtime). In a specific example of the dosing regimen 314 that includes multiple types of medications and referring now again to FIG. 5A—two 5-mg doses daily of amlodipine (e.g., one dose every 12 hours), plus two 81-mg doses daily of aspirin (e.g., one dose every 12 hours), plus two 20-mg doses daily of lisinopril (e.g., one dose every 12 hours), plus one 1000-mg dose daily of metformin IR (e.g., one dose upon waking), plus one 1000-mg dose daily of vitamin C (e.g., one mid-day dose), plus one 500-mg dose daily of cinnamon (e.g., one mid-day dose), plus one 75-mg dose daily of clopidogrel (e.g., one dose at bedtime), plus one 40-mg dose daily of furosemide (e.g., one dose at bedtime).

Further, in an example of the 30-day medication roll 250 wherein the patient's dosing regimen requires, for example, three medication packets 252 per day, 90 medication packets 252 is indicated in the dosing regimen 314. Additionally, the contents of each of the 90 medication packets 252 is indicated, in order by date and time, in the dosing regimen 314.

The dose detection algorithm 316 that is programmed into the processor 312 is used to detect valid dose events. For example, a dose event is deemed valid based on (1) sensing (e.g., via the micro-switch 132) the presence of the medication box 200 in the data-enabled medication box holder 100, and (2) sensing (e.g., via the reader/scanner device 324) the presence of the readable medium 260 on any medication packet 252 and capturing the contents thereof.

The security component 320 in the processor 312 can be any software module that is used to perform any security functions with respect to keeping secure the contents of, for example, the dosing regimen 314 and the actual dose information 318. For example, the security component 320 may use standard security techniques, such as encryption, secure hashtags (or hash tags), and the like. For example, the security component 320 can be used to decrypt the dosing regimen 314, which may be received encrypted. Additionally, the security component 320 can be used to encrypt the actual dose information 318 when transmitted via communications interface 310. However, the use of encryption in the data-enabled medication box holder 100 is optional.

The reader/scanner device 324 of the electronics module 126 of the data-enabled medication box holder 100 can be based on any reader/scanner technology that corresponds to the type of readable medium 260 provided on the medication packets 252 in the medication box 200. In one example, the reader/scanner device 324 can be an RFID reader for reading the RFID tags 262 on the medication packets 252. In this example, the processor 312 may include standard algorithms for processing the information read from the RFID tags 262. In another example, the reader/scanner device 324 can be an optical scanner (e.g., a digital camera) for reading the QR codes 264 on the medication packets 252. In this example, the processor 312 may include standard QR decoding algorithms for processing the image data and decoding the QR codes 264. In yet another example, the reader/scanner device 324 can be any standard barcode reader (or barcode scanner) technology for reading the barcodes 266 on the medication packets 252. Generally, a barcode reader includes a light source, a lens, and a light sensor that translates optical impulses into electrical signals. In this example, the processor 312 may include standard barcode decoding algorithms for processing the optical data and decoding the barcodes 266.

Optical scanner technology may require the presence of the optical window 130 in the platform 122, whereas RFID technology may not require the presence of the optical window 130. Further, the QR code technology and the barcode technology can be very directional; namely, a certain QR code 264 or certain barcode 266 can be read only when in the direct field of view of the reader/scanner device 324 at the platform 122. With respect to RFID technology, care must be taken to read only the RFID tag 262 in closest proximity to the RFID-based reader/scanner device 324 at the platform 122 and not those in the medication box 200. Accordingly, any RFID-based reader/scanner device 324 must be a low power, limited range, RFID scanner that is capable of capturing information from only the RFID tag 262 present in closest proximity to the platform 122. The processor 312 may be used to control the power/range of any RFID-based reader/scanner device 324.

Further, with respect to the first packet (i.e., also called the leader or header packet) of the medication roll 250, the leader packet (not shown) may not contain medication but, instead, may be a data packet that holds information that can be read/scanned via reader/scanner device 324. For example, the readable medium 260 of the leader packet can be programmed with information that can be used to initialize and/or configure the data-enabled medication box holder 100.

With respect to sensing the presence of the medication box 200 in the data-enabled medication box holder 100, the dose detection algorithm 316 of the processor 312 continuously monitors, for example, the state of the micro-switch 132. Accordingly, the state of the micro-switch 132 is one input of the dose detection algorithm 316 that is used for detecting valid dose events. For example, when the compartment 120 of the data-enabled medication box holder 100 is absent the medication box 200, the micro-switch 132 is not engaged. In this state, the micro-switch 132 output can be, for example, a logic "0." By contrast, when the medication box 200 is placed into the compartment 120, the medication box 200 engages the micro-switch 132. In so doing, the medication box 200 depresses the pushbutton of the micro-switch 132 and then the output of the micro-switch 132 toggles, for example, from the logic "0" to a logic "1." In this way, the micro-switch 132 is used to indicate to dose detection algorithm 316 the absence and presence of the medication box 200 in the compartment 120 of the data-enabled medication box holder 100.

With respect to sensing the presence of the readable medium 260 on any medication packet 252 and capturing the contents thereof, the dose detection algorithm 316 of the processor 312 continuously monitors the reader/scanner device 324 for data capture events. Accordingly, the output of the reader/scanner device 324 is another input of the dose detection algorithm 316 that is used for detecting valid dose events. For example, when any instance of readable medium 260 on any medication packet 252 is in close proximity the reader/scanner device 324, a data capture event occurs, which is detected by the dose detection algorithm 316. This can only happen when a user has pulled a medication packet 252 (a dose of medication) out of the medication box 200 and in close proximity to the platform 122 of the data-enabled medication box holder 100. In this way, the reader/scanner device 324 is used to indicate to the dose detection algorithm 316 the absence and presence of readable medium 260 at the platform 122 of the data-enabled medication box holder 100.

The presence of both the medication box 200 in the data-enabled medication box holder 100 and a data capture event of the reader/scanner device 324 indicates a valid dose event. Any valid dose events that are detected via dose detection algorithm 316 are logged in the actual dose information 318. For example, the date and time of the dose event and the contents of the medication packet 252 are logged in the actual dose information 318. More details of an example of a method of detecting a valid dose event are described with reference to FIG. 11.

Additionally, the processor 312 and/or the dose detection algorithm 316 can be programmed to compare valid dose events that are detected to information stored in the patient's dosing regimen 314. In so doing, it can be determined whether the prescribed dosing regimen is being followed. Namely, using the patient's dosing regimen 314, it can be determined whether doses have been taken on time, whether doses have been missed, whether extra doses have been taken, whether early doses have been taken, and whether late doses have been taken. Additionally, using the patient's dosing regimen 314, the processor 312 and/or the dose detection algorithm 316 can be used to activate reminder indicators and any other types of indicators. Namely, the real-time clock 322 provides a calendar and time of day function that can be used with the dosing regimen 314 in order to determine whether doses have been taken on time, whether doses have been missed, whether extra doses have been taken, whether early doses have been taken, and whether late doses have been taken, and to generate reminders. An example of the real-time clock 322 is the S-35390A, 2-wire CMOS real-time clock, available from Seiko Instruments, Inc (Torrance, Calif.).

The one or more indicators 128 are used to convey information to the patient or caretaker in response to the information processed via processor 312 and/or the dose detection algorithm 316. Further, the time-stamped states of any of the indicators 128 can also be logged in the actual dose information 318. In one example, the indicators 128 are LED devices. For example, four indicators 128 are provided—a green "TAKE" LED, a light green "TAKEN" LED, a red "MISSED" LED, and a yellow "ORDER REFILL" LED. The indicators 128 can be provided anywhere on the data-enabled medication box holder 100. In one example, the indicators 128 are provided on the front of the platform 122 of the data-enabled medication box holder 100. Further, TAKE, TAKEN, MISSED, and ORDER REFILL can be printed on the platform 122 corresponding to the four indicators 128. The indicators 128 can include other LEDs (not shown). Further, the LEDs can indicate things not directly related to the patient's medication adherence. For example, there can be a "CHECK BLOOD PRESSURE" LED, a "TIME FOR BLOOD WORK" LED, or a "MAKE A DOCTOR APPOINTMENT" LED, and the like. Further, the indicators 128 of the data-enabled medication box holder 100 are not limited to visual indicators (e.g., LEDs) only. The indicators 128 can include visual indicators (e.g., LEDs), audible indicators (beeping sounds), tactile indicators (vibration), digital displays, and any combinations thereof.

The green "TAKE" LED is used for prompting the user to take the prescribed dose of medication. For example, the information contained within the dosing regimen 314 may indicate a patient should take one dose at 4:00 pm daily. When the real-time clock 322 indicates the current time to be about 4:00 pm, the processor 312 activates the "TAKE" LED. In another example, if the dosing regimen 314 indicates 2 doses daily, 12 hours apart, then the "TAKE" LED may be activated about 12 hours after the previously detected valid dose event.

Upon detecting a valid dose event via dose detection algorithm 316, the "TAKE" LED is deactivated and the light green TAKEN" LED is activated. Namely, the "TAKEN" LED indicates that a valid dose event has occurred as detected via dose detection algorithm 316. For example, if all criteria of the dose detection algorithm 316 are met, the processor 312 activates the "TAKEN" LED. After the valid dose event is detected, the "TAKEN" LED may remain activated (e.g., continues to flash) for some period of time (e.g., an hour or until the next dose time).

The red "MISSED" LED indicates a user has not taken the dose of medication in accordance to the dosing regimen 314. Using the real-time clock 322, the processor 312 may be programmed to activate the "MISSED" LED, for example, one hour past the scheduled dose time. For example, the information contained within the dosing regimen 314 may indicate a patient should take one dose at 4:00 pm daily. In this example, when the real-time clock 322 indicates the current time is 5:00 pm and a dose event has not recently been detected via dose detection algorithm 316, the processor 312 activates the "MISSED" LED. The "MISSED" LED may remain activated for a predetermined period of time (e.g., 1 hour) or until the "TAKE" LED is next activated. Additionally, using the communications interface 310, a "missed dose alert" can be transmitted to the patient, caretaker, or any other authorized party.

The yellow "ORDER REFILL" LED indicates the medication box 200 is nearly out of medication and a prescription refill is needed. For example, a patient's dosing regimen may require three medication packets 252 per day for 30 days. Therefore, an initial fill of medication is 90 medication packets 252. The total number of medication packets 252 contained within the data-enabled medication box holder 100 (e.g., 90 medication packets 252) is indicated in the dosing regimen 314. The processor 312 can count the number of valid dose events logged in the actual dose information 318 and determine how many doses presently remain in the data-enabled medication box holder 100. In addition to dose count, the processor 312 uses real-time clock 322 to verify that, for example, at least 25 days have passed since the last refill (for a 30-day prescription), as health insurance companies typically will not authorize monthly refills until 25 days have passed since the last refill (for a 30-day prescription). In another example, for a 90-day prescription, the time period may be 85 days. Once the number of doses is nearly depleted (e.g., 5 doses remaining) and the prescribed number of days have passed (e.g., 25 days or 85 days), the processor 312 activates the "ORDER REFILL" LED to indicate that a refill is needed. Additionally, using the communications interface 310, a "refill alert" can be transmitted to the patient, caretaker, or any other authorized party.

FIG. 11 illustrates a flow diagram of a method 400, which is an example of a method of determining a valid dose event using the presently disclosed medication dispensing system 10 that includes the data-enabled medication box holder 100. In the method 400, a dose corresponds to one medication packet 252. The method 400 may include, but is not limited to, the following steps.

At a step 410, the processor 312 and/or the dose detection algorithm 316 monitor dose event criteria in order to detect valid dose events, track valid dose events, and communicate information about valid dose events and/or dose exception events. For example, the processor 312 and/or the dose detection algorithm 316 continuously monitor the state of the micro-switch 132, the output of the reader/scanner device 324, the calendar date and time of the real-time clock 322; all in relation to the patient's dosing regimen 314.

At a decision step 412, the processor 312 and/or the dose detection algorithm 316 determine whether the medication box 200 is present in the data-enabled medication box holder 100. Namely, the state of the micro-switch 132 indicates whether the medication box 200 is present in the compartment 120. For example, when the state of the micro-switch 132 is a logic "0," then the medication box 200 is not present in the compartment 120. However, when the state of the micro-switch 132 is a logic "1," then the medication box 200 is present in the compartment 120. If it is determined that the medication box 200 is present in the data-enabled medication box holder 100, the method 400 proceeds to a step 414. However, if it is determined that the medication box 200 is not present in the data-enabled medication box holder 100, then the method 400 returns to step 410.

At a decision step 414, the processor 312 and/or the dose detection algorithm 316 determine whether a data capture event of readable medium 260 has occurred at the reader/scanner device 324. For example, when any instance of readable medium 260 on any medication packet 252 is in close proximity the reader/scanner device 324, a data capture event occurs, which is detected by the dose detection algorithm 316. This can only happen when a user has pulled a medication packet 252 (a dose of medication) out of the medication box 200 and in close proximity to the platform 122 of the data-enabled medication box holder 100. If it is determined that a data capture event of readable medium 260 has occurred at the reader/scanner device 324, the method 400 proceeds to a step 416. However, if it is determined that a data capture event of readable medium 260 has not occurred at the reader/scanner device 324, then the method 400 returns to step 410.

At a step 416, a valid dose event is logged. Any valid dose events that are detected via dose detection algorithm 316 are logged in the actual dose information 318. For example, the date and time of the dose event and the contents of medication packet 252 is logged in the actual dose information 318.

FIG. 12 illustrates a flow diagram of a method 500, which is an example of a method of operation of the presently disclosed data-enabled medication box holder 100. Namely, the method 500 is a method of using the data-enabled medication box holder 100 for reminding at dose time and tracking and communicating valid dose events and/or dose exception events (e.g., missed, extra, early, and late doses). In the method 500, a dose corresponds to one medication packet 252. The method 500 may include, but is not limited to, the following steps.

At a step 510, the data-enabled medication box holder 100 is prepared for use. For example, using the communications interface 310, a medical or pharmaceutical professional, or other qualified party, may connect the data-enabled medication box holder 100 to a computer (not shown) for programming and exchange of information between the computer and the data-enabled medication box holder 100. For example, using the communications interface 310, the patient's dosing regimen 314 may be loaded into the processor 312, updates may be loaded into the dose detection algorithm 316, the real-time clock 322 may be set or reset, the health status of the battery may be checked, and the like. In another example, because the data-enabled medication box holder 100 can be connected to a network, the data-enabled medication box holder 100 can be configured by remote access. Further, the medication roll 250 of multiple medication packets 252 that contain the prescribed medication (i.e., a medication roll 250 that is customized to the patient) is placed in the medication box 200. Then, the medication box 200 is labeled and physically conveyed to the patient for use. The method 500 proceeds to step 512.

At a step 512, the processor 312 and/or the dose detection algorithm 316 monitor dose event criteria and medication adherence continuously or at specified intervals. For example, the processor 312 receives and interprets information from the dosing regimen 314, the dose detection algorithm 316, the real-time clock 322, whether and when valid dose events occur and whether they are in compliance with/adherent to prescribed dosing instructions stored in the dosing regimen 314. Further, at any time, the patient can visually monitor the indicators 128 to see whether any action is required, such as whether it is time to take a dose, whether a dose has been missed, whether it is time for a prescription refill, and the like. The method 500 proceeds to step 514.

At an optional step 514, encrypted or unencrypted the actual dose information 318 is transmitted to an external computing device using the communications interface 310. Namely, at any time during the method 400, any information at the data-enabled medication box holder 100 can be interrogated using the communications interface 310. The method 500 proceeds to step 516.

At a step 516, any previously activated indicators 128 are deactivated, the "TAKE" LED is activated according to the dosing regimen 314, and this event is logged in the actual dose information 318. Optionally, using the communications interface 310, a "take dose alert" can be transmitted to the patient or any other caretaker or authorized party that it is time to take the dose. The method 500 proceeds to step 518.

At a decision step 518, it is determined whether a valid dose event has occurred according to the method 400. If it is determined that a valid dose event has occurred, the method 500 proceeds to step 522. However, if it is determined that a valid dose event has not occurred within the prescribed period of time (e.g., within ±2 hours of the prescribed time), then the method 500 proceeds to step 520.

At a step 520, any previously activated indicators 128 are deactivated, the "MISSED" LED is activated, and this event is logged in the actual dose information 318. Optionally, using the communications interface 310, a "missed dose alert" can be transmitted to the patient or any other caretaker or authorized party that the dose has been missed. The method 500 returns to step 518.

At a step 522, once a valid dose event has been detected according to the method 400, any previously activated indicators 128 are deactivated, the "TAKEN" LED is activated, and this event is logged in the actual dose information 318. Optionally, using the communications interface 310, a "dose taken alert" can be transmitted to the patient, the pharmacy, or any other caretaker or authorized party. The method 500 proceeds to both step 524 and step 528.

At a decision step 524, it is determined whether a prescription refill is needed. For example, the processor 312 can count the number of valid dose events logged in the actual dose information 318 and determine how many doses (i.e., medication packets 252) presently remain in the data-enabled medication box holder 100. In addition to dose count, the processor 312 uses real-time clock 322 to verify that, for example, at least 25 days have passed since the last refill (for a 30-day prescription). In another example, for a 90-day prescription, the time period may be 85 days. If the processor 312 determines that the number of doses is nearly depleted (e.g., 5 doses remaining) and the prescribed number of days have passed (e.g., 25 days or 85 days), then method a prescription refill is needed and the method 500 proceeds to step 526. However, if the processor 312 determines that the number of doses is not nearly depleted (e.g., greater than 5 doses remaining) or that the prescribed number of days have not passed, then a prescription refill is not needed and the method 500 returns to step 512.

At a step 526, any previously activated indicators 128 are deactivated, the "ORDER REFILL" LED is activated, and this event is logged in the actual dose information 318. Optionally, using the communications interface 310, a "refill alert" can be transmitted to the patient, the pharmacy, or any other caretaker or authorized party. The method 500 returns to step 512.

At a decision step 528, it is determined whether an extra dose event has occurred according to the method 400 and according to the dosing regimen in the patient's dosing regimen 314. If it is determined that an extra dose event has occurred, the method 500 proceeds to step 530. However, if it is determined that an extra dose event has not occurred with respect to the dosing regimen in the patient's dosing regimen 314, then the method 500 returns to step 512.

At a step 530, the extra dose event is logged in the actual dose information 318. Optionally, using the communications interface 310, an "extra dose alert" can be transmitted to the patient, the pharmacy, or any other caretaker or authorized party. Optionally, the electronics module 126 can include an "EXTRA DOSE" LED that is activated in this step. The method 500 returns to step 512.

Table 1 below shows an example of a record of data in the actual dose information 318 that can be compiled using the method 400 of FIG. 11 and/or the method 500 of FIG. 12. In the example shown in Table 1, the record of data is for one calendar day.

TABLE 1

Example record of data in the actual dose information 318 for Apr. 11, 2016

Patient Name: John Doe
Patient Address: 487 Elm St, Scranton, PA 18505
RX# 0569790-07365

| Medication | Dose | Dose Time |
|---|---|---|
| Amlodipine | two 5-mg doses daily | 08:00, 20:00 |
| Aspirin | two 81-mg doses daily | 08:00, 20:00 |
| Lisinopril | two 20-mg doses daily | 08:00, 20:00 |
| Metformin IR | one 1000-mg dose daily | 08:00 |
| Vitamin C | one 1000-mg dose daily | 13:00 |
| Cinnamon | one 500-mg dose daily | 13:00 |
| Clopidogrel | one 75-mg dose daily | 20:00 |
| Furosemide | one 40-mg dose daily | 20:00 |

| Timestamp Data | Event Data | Medication packet ID | Medication packet contents |
|---|---|---|---|
| 11-Apr-2016; 08:00:00.0 | "TAKE" LED activated | | |
| 11-Apr-2016; 09:00:00.0 | "MISSED" LED activated | | |
| 11-Apr-2016; 09:51:15.7 | Valid dose event detected, "MISSED" LED deactivated, "TAKEN" LED activated | 396852B31 | 5-mg amlodipine 81-mg aspirin 20-mg lisinopril 1000-mg metformin IR |
| 11-Apr-2016; 10:51:15.7 | "TAKEN" LED deactivated | | |
| 11-Apr-2016; 13:00:00.0 | "TAKE" LED activated | | |
| 11-Apr-2016; 13:17:55.8 | Valid dose event detected, "TAKE" LED deactivated, "TAKEN" LED activated | 396852B32 | 1000-mg vitamin C 500-mg cinnamon |
| 11-Apr-2016; 14:17:55.8 | "TAKEN" LED deactivated | | |
| 11-Apr-2016; 20:00:00.0 | "TAKE" LED activated | | |

TABLE 1-continued

Example record of data in the actual dose information 318 for Apr. 11, 2016

| | | | |
|---|---|---|---|
| 11-Apr-2016; 20:38:06.2 | Valid dose event detected, "TAKE" LED deactivated, "TAKEN" LED activated | 396852B33 | 5-mg amlodipine 81-mg aspirin 20-mg lisinopril 75-mg clopidogrel 40-mg furosemide |
| 11-Apr-2016; 21:38:06.2 | "TAKEN" LED deactivated | | |

While the example shown in Table 1 is a record of data is for one calendar day, the actual dose information 318 can include any number of records, for any number of days. For example, Table 2 below shows an example of a summary report for a 30-day period for one specific medication (e.g., LEVOTHYROXINE), wherein the summary report is compiled using information in the actual dose information 318. Table 2 also shows the percent medication adherence for the patient for the 30-day period with respect to LEVOTHYROXINE.

TABLE 2

Example summary report for a 30-day period: LEVOTHYROXINE

Patient Name: John Doe
Patient Address: 487 Elm St, Scranton, PA 18505
RX# 0569790-07365
Medication: LEVOTHYROXINE
Start: Oct. 15, 2016
Duration: 30 days
Dose: One 50-mg dose daily
Dose Time: 08:00 ± 2 hours
Summary: Taken = 24 doses, Missed = 6 doses, Adherence = 80%

| Day | Date | Time | Status |
|---|---|---|---|
| Saturday | 10/15/2016 | 07:58 | Taken |
| Sunday | 10/16/2016 | 09:05 | Taken |
| Monday | 10/17/2016 | 10:01 | Missed |
| Monday | 10/17/2016 | 13:05 | Late |
| Tuesday | 10/18/2016 | 06:30 | Taken |
| Wednesday | 10/19/2016 | 08:15 | Taken |
| Thursday | 10/20/2016 | 07:45 | Taken |
| Friday | 10/21/2016 | 07:51 | Taken |
| Saturday | 10/22/2016 | 10:01 | Missed |
| Sunday | 10/23/2016 | 10:01 | Missed |
| Monday | 10/24/2016 | 10:01 | Missed |
| Tuesday | 10/25/2016 | 08:30 | Taken |
| Wednesday | 10/26/2016 | 06:15 | Taken |
| Wednesday | 10/26/2016 | 09:37 | Extra |
| Thursday | 10/27/2016 | 07:32 | Taken |
| Friday | 10/28/2016 | 07:34 | Taken |
| Saturday | 10/29/2016 | 08:12 | Taken |
| Sunday | 10/30/2016 | 09:15 | Taken |
| Monday | 10/31/2016 | 09:57 | Taken |
| Tuesday | 11/01/2016 | 07:25 | Taken |
| Wednesday | 11/02/2016 | 09:21 | Taken |
| Thursday | 11/03/2016 | 07:43 | Taken |
| Friday | 11/04/2016 | 08:09 | Taken |
| Saturday | 11/05/2016 | 05:44 | Early |
| Saturday | 11/06/2016 | 10:01 | Missed |
| Sunday | 11/06/2016 | 07:19 | Taken |
| Monday | 11/07/2016 | 10:01 | Missed |
| Tuesday | 11/08/2016 | 10:01 | Missed |
| Wednesday | 11/09/2016 | 10:01 | Missed |
| Thursday | 11/10/2016 | 07:34 | Taken |
| Friday | 11/11/2016 | 08:42 | Taken |
| Saturday | 11/12/2016 | 09:48 | Taken |
| Sunday | 11/13/2016 | 09:01 | Taken |

FIG. 13 illustrates a block diagram of a medication adherence system 600 for monitoring a patient's medication adherence and facilitating dose reminder notifications according to one embodiment of the invention. The medication adherence system 600 is based on the medication dispensing system 10 that includes the data-enabled medication box holder 100 and the medication box 200, as described hereinabove with reference to FIG. 1 through FIG. 12. Further, in medication adherence system 600, communication is facilitated primarily via a cellular network.

The medication adherence system 600 includes an application server 610. The application server 610 can be any centralized server or computer that is accessible via a network. In one example, the application server 610 is a cloud server. Residing at the application server 610 is a medication adherence application 612 and a database 614. Stored at the database 614 are, for example, subscription data 616, summary reports 618, and exception reports 620.

The medication adherence system 600 also includes the data-enabled medication box holder 100 and the medication box 200. The data-enabled medication box holder 100 includes mechanisms for reminding at dose time, tracking and communicating valid dose events, as well as missed, extra, early, and/or late dose events. The data-enabled medication box holder 100 includes control electronics (i.e., electronics module 126) for processing and communicating information about valid dose events, missed dose events, and/or extra dose events. For example, using the processor 312 and the dose detection algorithm 316 according to the method 400 of FIG. 11, a dose event is deemed valid based on (1) sensing (e.g., via the micro-switch 132) the presence of the medication box 200 in the data-enabled medication box holder 100, and (2) sensing (e.g., via the reader/scanner device 324) the presence of the readable medium 260 on any medication packet 252 and capturing the contents thereof.

The medication adherence system 600 also includes a mobile phone 640. The mobile phone 640 can be any mobile phone that is capable of (1) running mobile applications, (2) communicating with the data-enabled medication box holder 100, and (3) communicating with the application server 610 (through the internet and/or the cellular network). The mobile phone 640 can be, for example, an Android™ phone, an Apple iPhone, or a Samsung Galaxy phone. The mobile phone 640 can also be any other mobile device that has cellular network capability, such as a cellular-enabled tablet device (e.g., an Apple iPad). Further, while FIG. 13 shows the data-enabled medication box holder 100 communicating with the application server 610 through the mobile phone 640, in other embodiments the data-enabled medication box holder 100 can communicate directly with the application server 610, absent the mobile phone 640.

In medication adherence system 600, a medication adherence mobile app 642 is running on the mobile phone 640. The medication adherence mobile app 642 is the counterpart to the medication adherence application 612 that is running at the application server 610. The data-enabled medication box holder 100 and the mobile phone 640 belong to a patient 650 that is associated with the medication adherence system 600.

In the medication adherence system 600, the patient 650's data-enabled medication box holder 100 can transmit information wirelessly to the patient's mobile phone 640. Then, the patient's mobile phone 640 is used to transmit (via a cellular network 660) the patient-specific information to the application server 610, wherein the application server 610 is used for collecting and processing patient-specific information from the data-enabled medication box holder 100.

The medication adherence system 600 is not limited to one patient 650 and his/her one data-enabled medication box holder 100 and one mobile phone 640. The medication adherence system 600 can support any number of patients 650, data-enabled medication box holders 100, and mobile phones 640, wherein the application server 610 collects and processes patient-specific information from multiple patients 650. Further, any given patient 650 can have multiple data-enabled medication box holders 100, which correspond to multiple medication prescriptions. In one example, the medication adherence system 600 can be implemented in a client-server type of system architecture, wherein the mobile phones 640 are the clients and the application server 610 is the server.

Further, the medication adherence system 600 can be a subscription-based system, wherein patients 650 subscribe to the medication adherence system 600 in order to download the medication adherence mobile app 642 to their mobile phones 640 and to take advantage of the functionality of the medication adherence application 612 at application server 610. The subscription data 616 in the database 614 at the application server 610 may contain, for example, patient names, patient account information, patient credentials, patient profiles, a record of the patient's prescriptions, and the like. The exception reports 620 in the database 614 are patient-specific exception information, wherein examples of exceptions include, but are not limited to, missed doses, extra doses, early doses, and late doses. The medication adherence application 612 determines patient-specific exceptions and generates patient-specific summary reports 618 by analyzing patient-specific information that is generated at each patient 650's data-enabled medication box holder 100 and then transmitted to application server 610 via each patient 650's mobile phone 640.

Associated with the medication adherence system 600 are one or more notifiers 655. In one example, when an exception occurs (e.g., missed, extra, early, or late dose), notifiers 655 can be any authorized personnel that are tasked to contact the patient 650 and notify them of the exception. Associated with the one or more notifiers 655 are their respective communication devices 660. The communication device 660 is, for example, a mobile phone, a landline phone, or any computing device. For example, using a telephone, a notifier 655 can call a certain patient 650 and notify him/her that a dose of medication was recently missed, thereby providing a reminder to get caught up on his/her dosing regimen. In another example, exception notifications can be automatically transmitted electronically to the patient 650, such as via email or text message. The communication devices 660 of the notifiers 655 can be connected to the application server 610 via the cellular network 660 or optionally via a network 670. The network 670 can be any network for providing wired or wireless connection to the Internet, such as a local area network (LAN) or a wide area network (WAN).

FIG. 14 illustrates a block diagram of a medication adherence system 700 for monitoring a patient's medication adherence and facilitating dose reminder notifications according to another embodiment of the invention. Namely, in medication adherence system 700, communication is facilitated primarily via the Internet. That is, the medication adherence system 700 is substantially the same as the medication adherence system 600 of FIG. 13, except that the cellular network 660 is replaced with the network 670. Further, the mobile phones 640 with their medication adherence mobile apps 642 are replaced with computing devices 740, wherein each of the computing devices 740 has a mobile/desktop medication adherence application 742 running thereon. The computing devices 740 can be, for example, desktop computers, laptop computers, handheld computing devices, mobile phones, personal digital assistants (PDAs), and tablet devices. The computing devices 740 have wireless communication capabilities for communicating with the data-enabled medication box holders 100. For example, the computing device 740 is Bluetooth®-enabled and/or Wi-Fi-enabled for communicating wirelessly with other local devices, such as the data-enabled medication box holder 100. The computing device 740 can be, for example, an Apple iPad.

Like the medication adherence mobile app 642 of FIG. 13, the mobile/desktop medication adherence application 742 is the counterpart to the medication adherence application 612 that is running at the application server 610.

FIG. 15 illustrates a flow diagram of an example of a method 800 of using the presently disclosed medication adherence system 600 and/or 700 for monitoring a patient 650's medication adherence and facilitating dose reminder notifications. Method 800 may include, but is not limited to, the following steps.

At a step 810, the data-enabled medication box holder 100 logs dosing activity in actual dose information 318. For example, the processor 312 and/or the dose detection algorithm 316 continuously monitor the state of the micro-switch 132 and the output of the reader/scanner device 324, if both the medication box 200 is present in the data-enabled medication box holder 100 and a data capture event of the reader/scanner device 324 is present, a time-stamped valid dose event is logged in the actual dose information 318. The valid dose events that are detected can be compared to information in the patient's dosing regimen 314 in order to determine whether the prescribed dosing regimen is being followed. Namely, using the patient's dosing regimen 314, it can be determined whether doses are taken on time, whether doses have been missed, whether extra doses have been taken, whether early doses have been taken, and/or whether late doses have been taken. Further, the time-stamped states of any of the indicators 128 can also be logged in the actual dose information 318. An example of dosing activity that can be logged in actual dose information 318 is shown above in Table 1.

At a step 812, the contents of the actual dose information 318 is transmitted from the data-enabled medication box holder 100 to the network-enabled communication device, such as the mobile phone 640 or the computing device 740. The method 800 proceeds to a step 814.

In one example, the data-enabled medication box holder 100 periodically pushes the contents of the actual dose information 318 to the mobile phone 640 or to the computing device 740. For example, using Bluetooth technology in the communications interface 310, the processor 312 of the data-enabled medication box holder 100 is programmed to push the actual dose information 318 once per day, twice per day, three times per day, or four times per day to the medication adherence mobile app 642 of the mobile phone 640 and/or to the mobile/desktop medication adherence application 742 of the computing device 740.

In another example, the data-enabled medication box holder 100 pushes the contents of the actual dose information 318 in real time to the mobile phone 640 or to the computing device 740. For example, using Bluetooth technology in the communications interface 310, the processor 312 of the data-enabled medication box holder 100 is programmed to push the actual dose information 318 to the medication adherence mobile app 642 of the mobile phone 640 and/or to the mobile/desktop medication adherence application 742 of the computing device 740 anytime that the actual dose information 318 is updated.

In yet another example, the mobile phone 640 and/or the computing device 740 periodically pull the contents of the actual dose information 318 from the data-enabled medication box holder 100. For example, using Bluetooth technology, the medication adherence mobile app 642 of the mobile phone 640 and/or the mobile/desktop medication adherence application 742 of the computing device 740 are programmed to periodically pull the actual dose information 318 from the data-enabled medication box holder 100. The method 800 proceeds to a step 814.

At a step 814, using the cellular network 660 and/or the network 670, the actual dose information 318 is transmitted from the patient 650's network-enabled communication device to the application server 610. For example, the actual dose information 318 is transmitted from the medication adherence mobile app 642 of the patient 650's mobile phone 640 and/or the mobile/desktop medication adherence application 742 of the patient 650's computing device 740 to the medication adherence application 612 of the application server 610. Optionally, both the patient 650's actual dose information 318 and dosing regimen 314 are transmitted from the patient 650's mobile phone 640 or computing device 740 to the application server 610. The method 800 proceeds to a step 816.

At a step 816, the medication adherence application 612 of the application server 610 processes the patient-specific actual dose information 318 received from the patient 650's mobile phone 640 or computing device 740. The method 800 proceeds to a step 818 and to a step 820.

At a step 818, using the contents of the patient-specific actual dose information 318, a patient-specific summary report 618 is compiled. An example of a patient-specific summary report 618 is shown above in Table 2.

At a decision step 820, it is determined whether any exceptions are indicated the patient-specific actual dose information 318. For example, it is determined whether any missed doses, extra doses, early doses and/or late doses are indicated the patient-specific actual dose information 318. If at least one exception is indicated, then the method proceeds to a step 822. However, if no exceptions are indicated, then the method returns to a step 816.

At a step 822, exception information is logged in a patient-specific exception report 620 and a notification of the exception is transmitted to a notifier 655. An example of a patient-specific exception report 620 is shown above in Table 3. For example, a certain notifier 655 is notified (via email, text message, etc.) that a certain patient 650 missed a dose of medication.

At a step 824, a notifier 655 and/or the medication adherence application 612 notifies the patient 650 of the dose exception, such as missed dose, extra dose, early dose, and late dose. In one example, at step 812, the data-enabled medication box holder 100 is programmed to push the actual dose information 318 to the patient 650's mobile phone 640 or computing device 740 once per day at midnight. Then, at step 814 the patient 650's mobile phone 640 or computing device 740 transmits the patient-specific actual dose information 318 to the medication adherence application 612 at the application server 610. Then, the next day, a notifier 655 and/or the medication adherence application 612 notifies the patient 650 of, for example, a missed dose. In one example, the next day, the notifier 655 notifies the patient 650 by telephone of the previous day's missed dose. In another example, the next day, the notifier 655 notifies the patient 650 by email or text message of the previous day's missed dose. In yet another example, the next day, the medication adherence application 612 automatically transmits an "exception" notification, such as a "missed dose" notification, to the patient 650 via, for example, email or text message.

FIG. 16 illustrates a block diagram of a medication adherence system 900 for monitoring a patient's medication adherence and facilitating dose reminder notifications according to yet another embodiment of the invention. Namely, in medication adherence system 900, communication is facilitated primarily via a landline. That is, the medication adherence system 900 is substantially the same as the medication adherence system 600 of FIG. 13, except that the mobile phones 640 and the cellular network 660 are replaced with a Bluetooth landline (or dial-up) modem 910 and the application server 610 is a dial-in server. The Bluetooth landline (or dial-up) modem 910 provides both landline dial-up capability for communicating with the dial-in application server 610 and Bluetooth technology for communicating with the data-enabled medication box holder 100. Examples of the Bluetooth landline (or dial-up) modem 910 include, but are not limited to, the Sitecom CN-503 Bluetooth Modem available from Sitecom Europe BV (Rotterdam, Zuid-Holland) and the Model 4300 Zoom Bluetooth Modem available from Zoom Telephonics Inc. (Boston, Mass.).

In the medication adherence system 900, the processor 312 may be programmed to transmit the actual dose information 318 and optionally the dosing regimen 314 to the dial-in application server 610 once per day, such as at midnight. For example, the data-enabled medication box holder 100 communicates via Bluetooth technology with the Bluetooth landline (or dial-up) modem 910 to initiate a dial-up operation, then transmits the contents of the actual dose information 318 and optionally the dosing regimen 314 to the dial-in application server 610 over a landline.

In still another embodiment of the presently disclosed medication adherence systems 600, 700, 900, the medication adherence systems utilize the cellular network 660, the network 670, the Bluetooth landline (or dial-up) modem 910, and any combinations thereof.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A data-enabled medication dispensing system, comprising:
    a. data-enabled medication box holder, comprising:
        i. a housing comprising a compartment configured to at least partially receive a medication box comprising medication packets having machine-readable medium;
        ii. a sensing mechanism integrated with the compartment for sensing the presence or absence of the medication box therein;
        iii. an electronics module integrated with the housing, wherein the electronics module is configured for providing a reminder at dose time and monitoring, tracking, and communicating valid dose events and/or dose exception events, and wherein the electronic module comprises a reader configured to read the machine-readable medium associated with each of the medication packets, and wherein the reader is positioned such that the reader is capable of reading the readable medium of an individual medication packet being removed after at least a portion of the individual medication packet being removed is exterior of the housing; and
        iv. one or more indicators electronically coupled to the electronics module;
    b. a medication box received in the compartment; and
    c. a server in communication with the electronics module of the medication box holder, wherein the server is configured for collecting and processing patient-specific information communicated from the electronics control module of the data-enabled medication box holder.

2. The data-enabled medication dispensing system of claim 1, wherein the server comprises a medication adherence application and a database, wherein the database stores one or more of prescription data, summary reports, and exception reports.

3. A method of determining a valid dose event using a data-enabled medication dispensing system, the method comprising:
    a. providing a data-enabled medication box holder comprising:
        i. a housing comprising a compartment configured to at least partially receive a medication box comprising medication packets having machine-readable medium;
        ii. a sensing mechanism integrated with the compartment for sensing the presence or absence of the medication box therein;
        iii. an electronics module integrated with the housing, wherein the electronics module is configured for providing a reminder at dose time and monitoring, tracking, and communicating valid dose events and/or dose exception events, and wherein the electronics module comprises a reader configured to read the machine-readable medium of the medication packets, and wherein the reader is positioned such that the reader is capable of reading the readable medium of an individual medication packet being removed after at least a portion of the individual medication packet being removed is exterior of the housing; and
        iv. one or more indicators electronically coupled to the electronics module;
    b. monitoring the data-enabled medication box holder for pre-defined valid dose event criteria, wherein the pre-defined valid dose event criteria comprises determining if a medication box is present in the data-enabled medication box holder and reading/scanning the machine-readable medium of the medication packet and capturing the contents thereof;
    c. determining whether the data-enabled medication box holder has met the pre-defined criteria for the valid dose event; and
    d. recording the valid dose event upon determining the pre-defined criteria for the valid dose event is met.

4. A method of using a data-enabled medication box holder for reminding at dose time and monitoring, tracking, and communicating valid dose events and/or dose exception events, the method comprising:
    a. preparing the data-enabled medication box holder for use wherein the data-enabled medication box holder comprises:
        i. a housing comprising a compartment configured to at least partially receive a medication box comprising medication packets having machine-readable medium;
        ii. a sensing mechanism integrated with the compartment for sensing the presence or absence of the medication box therein;
        iii. an electronics module integrated with the housing, wherein the electronics module is configured for providing a reminder at dose time and monitoring, tracking, and communicating valid dose events and/ or dose exception events, and wherein the electronics module comprises a reader configured to read the machine-readable medium of the medication packets, and wherein the reader is positioned such that the reader is capable of reading the readable medium of an individual medication packet being removed after at least a portion of the individual medication packet being removed is exterior of the housing; and iv. one or more indicators electronically coupled to the electronics module;

b. monitoring valid dose event criteria and medication adherence;

c. determining whether a valid dose event has occurred, wherein the valid dose event comprises sensing the medication box is present in the data-enabled medication box holder and reading/scanning the machine-readable medium of the medication packet and capturing the contents thereof; and d. recording actual dose event data.

5. The method of claim 4 wherein preparing the data-enabled medication box holder for use comprises one or more of programming a patient's dosing regimen into a processor of the data-enabled medication box holder; and inserting a medication box into the data-enabled medication box holder.

6. The method of claim 5 wherein monitoring valid dose event criteria and medication adherence comprises the processor receiving and interpreting data from one or more of the patient's dosing regimen; a dose detection algorithm; a real-time clock; whether and when valid dose events occur and whether they are in compliance with/adherent to dosing instructions stored in the patient's dosing regimen.

7. The method of claim 4 wherein the one or more indicators are capable of being monitored by a patient, and are configured to indicate to the patient at least one of, time to take a dose, a dose has been missed, and time for a prescription refill.

8. The method of claim 4 further comprising transmitting data from the data-enabled medication box holder to an external computing device using a communications interface.

9. The method of claim 8 wherein data from the data-enabled medication box holder is transmitted to one or more of a patient, caretaker, pharmacist, and an authorized party via a communications interface.

* * * * *